United States Patent
Antaris et al.

(10) Patent No.: US 12,369,797 B2
(45) Date of Patent: Jul. 29, 2025

(54) SYSTEMS AND A METHOD FOR DIRECTING AN IMAGING DEVICE TO DETECT FLUORESCENCE AND FOR DETERMINING A LIFETIME OF THE FLUORESCENCE

(71) Applicant: Intuitive Surgical Operations, Inc., Sunnyvale, CA (US)

(72) Inventors: Alexander L. Antaris, Emerald Hills, CA (US); Jeffrey M. DiCarlo, Austin, TX (US); Ian E. McDowall, Woodside, CA (US); Jonathan M. Sorger, Belmont, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 542 days.

(21) Appl. No.: 17/635,988

(22) PCT Filed: Aug. 18, 2020

(86) PCT No.: PCT/US2020/046817
§ 371 (c)(1),
(2) Date: Feb. 16, 2022

(87) PCT Pub. No.: WO2021/034838
PCT Pub. Date: Feb. 25, 2021

(65) Prior Publication Data
US 2022/0280042 A1    Sep. 8, 2022

Related U.S. Application Data

(60) Provisional application No. 62/889,433, filed on Aug. 20, 2019.

(51) Int. Cl.
*A61B 5/00* (2006.01)
*A61B 34/00* (2016.01)
*A61B 90/00* (2016.01)

(52) U.S. Cl.
CPC ............ *A61B 5/0071* (2013.01); *A61B 34/00* (2016.02); *A61B 90/37* (2016.02)

(58) Field of Classification Search
None
See application file for complete search history.

(56) References Cited

U.S. PATENT DOCUMENTS

2005/0048539 A1* 3/2005 Hyman ................ G01N 33/542
435/7.1
2009/0164130 A1* 6/2009 Kumar ............... G01N 21/6408
702/19

(Continued)

FOREIGN PATENT DOCUMENTS

WO    WO-2018065456 A1    4/2018

OTHER PUBLICATIONS

International Search Report and Written Opinion for Application No. PCT/US2020/046817, mailed Jan. 18, 2021, 16 pages.

(Continued)

*Primary Examiner* — Patricia J Park

(57) ABSTRACT

An exemplary fluorescence imaging control system may direct, during a surgical procedure performed with a computer-assisted surgical system, an illumination source included in the computer-assisted surgical system to illuminate a scene associated with the surgical procedure with fluorescence excitation illumination configured to excite a fluorophore present at the scene and direct an imaging device included in the computer-assisted surgical system to detect, during the surgical procedure, fluorescence emitted by the fluorophore in response to excitation of the fluorophore by the fluorescence excitation illumination. The fluorescence imaging control system may determine, based on the detected fluorescence, a lifetime of the fluorescence and determine, based on the determined lifetime of the fluorescence, an identity of the fluorophore. The fluorescence (Continued)

imaging control system may configure, during the surgical procedure and based on the determined identity of the fluorophore, operation of the computer-assisted surgical system.

20 Claims, 10 Drawing Sheets

(56)  References Cited

U.S. PATENT DOCUMENTS

| | | |
|---|---|---|
| 2009/0227043 A1 | 9/2009 | Huang |
| 2011/0178412 A1 | 7/2011 | Orlewski |
| 2013/0155499 A1* | 6/2013 | Dixon .................. G02B 21/367 |
| | | 359/385 |
| 2013/0183676 A1* | 7/2013 | Chen .................. G01N 21/6408 |
| | | 435/6.12 |
| 2014/0378843 A1* | 12/2014 | Valdes .................. A61B 1/063 |
| | | 600/476 |
| 2016/0133668 A1* | 5/2016 | Rothberg ............. H04N 25/771 |
| | | 250/206 |
| 2020/0323431 A1* | 10/2020 | St. John ................. A61B 5/444 |

OTHER PUBLICATIONS

Invitation to Pay Additional Fees mailed on Nov. 16, 2020 for PCT Application No. PCT/US2020/046817 filed on Aug. 18, 2020, 10 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

International Preliminary Report on Patentability for Application No. PCT/US2020/046817, mailed Mar. 3, 2022, 10 pages.

* cited by examiner

SYSTEMS AND A METHOD FOR DIRECTING AN IMAGING DEVICE TO DETECT FLUORESCENCE AND FOR DETERMINING A LIFETIME OF THE FLUORESCENCE

RELATED APPLICATIONS

The present application is a U.S. National Stage Application under 35 U.S.C. § 371 of International Application No. PCT/US2020/046817, filed on Aug. 18, 2020, which claims priority to U.S. Provisional Patent Application No. 62/889,433, filed on Aug. 20, 2019, the contents of which are hereby incorporated by reference in their entirety.

BACKGROUND INFORMATION

An imaging device (e.g., an endoscope) may be used during a surgical procedure to capture images of a surgical area associated with a patient. The images may be presented (e.g., in the form of a video stream) to a surgeon during the surgical procedure to assist the surgeon in performing the surgical procedure. In some scenarios the images of the surgical area may include or be augmented with other captured images, such as fluorescence images. Fluorescence images are generated based on detected fluorescence emitted by a fluorophore upon excitation by a light source. The fluorescence images may be used, for example, to highlight certain portions of the surgical area in a selected color (e.g., green).

There are many available fluorophores for use, and new fluorophores are continually being developed. However, there remains room to improve and expand the use of fluorescence imaging in medical imaging.

SUMMARY

The following description presents a simplified summary of one or more aspects of the methods and systems described herein in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

An exemplary system may comprise a memory storing instructions; and a processor communicatively coupled to the memory and configured to execute the instructions to direct an illumination source to illuminate a scene with fluorescence excitation illumination configured to excite a fluorophore present at the scene; direct an imaging device to detect fluorescence emitted by the fluorophore in response to excitation of the fluorophore by the fluorescence excitation illumination; determine, based on the detected fluorescence, a lifetime of the fluorescence; and determine, based on the determined lifetime of the fluorescence, an identity of the fluorophore.

Another exemplary system may comprise a memory storing instructions; and a processor communicatively coupled to the memory and configured to execute the instructions to direct an illumination source to illuminate a scene with fluorescence excitation illumination configured to excite a fluorophore present in tissue at the scene; direct an imaging device to detect fluorescence emitted by the fluorophore in response to excitation of the fluorophore by the fluorescence excitation illumination; determine, based on the detected fluorescence; a lifetime of the fluorescence; and determine, based on the determined lifetime of the fluorescence, a type of the tissue in which the fluorophore is present.

An exemplary method may comprise directing, by a fluorescence imaging control system, an illumination source to illuminate a scene with fluorescence excitation illumination configured to excite a fluorophore present at the scene; directing, by the fluorescence imaging control system, an imaging device to detect fluorescence emitted by the fluorophore in response to excitation of the fluorophore by the fluorescence excitation illumination; determining, by the fluorescence imaging control system based on the detected fluorescence, a lifetime of the fluorescence; and determining, by the fluorescence imaging control system based on the determined lifetime of the fluorescence; an identity of the fluorophore.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
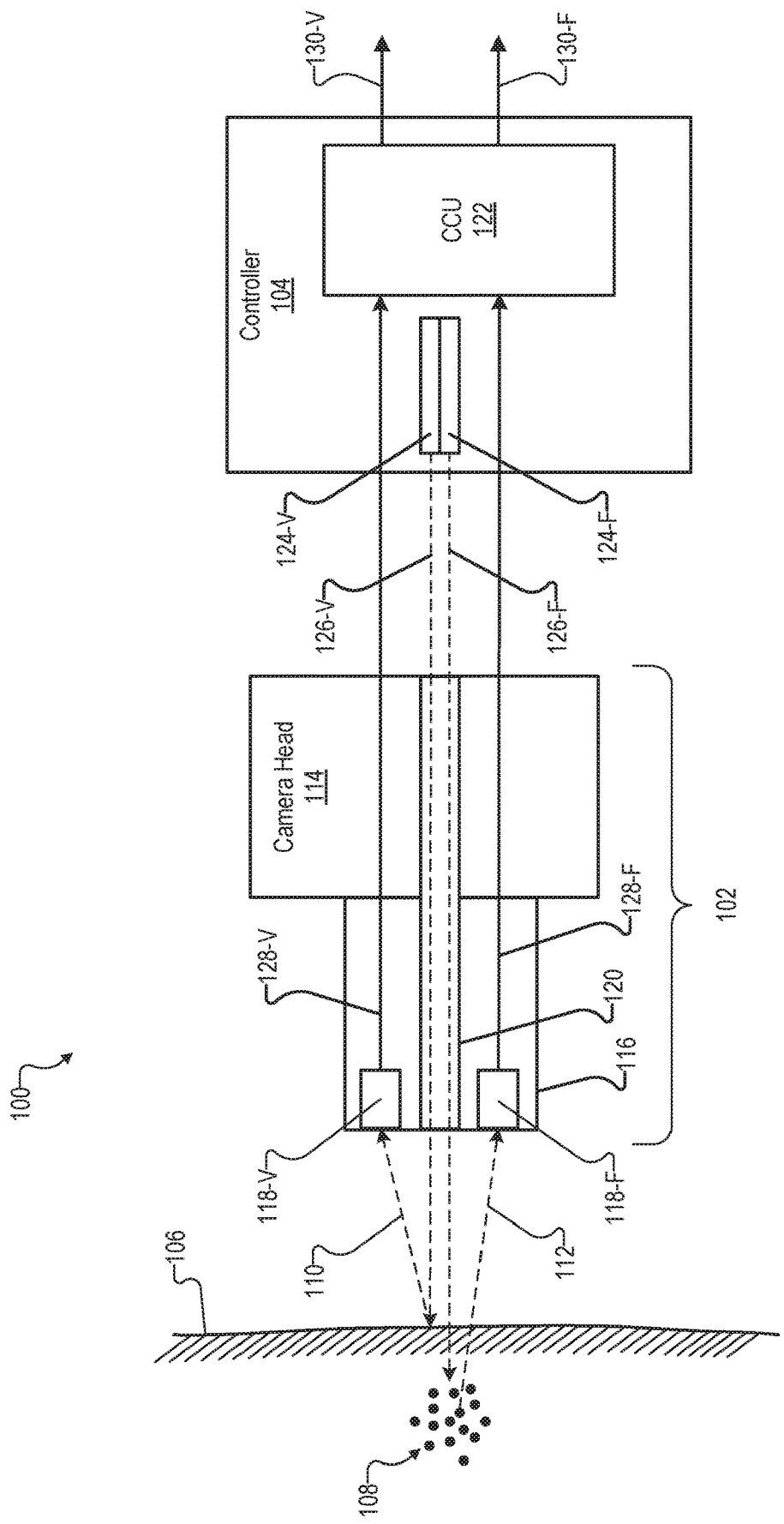
FIG. 1 illustrates an exemplary imaging system according to principles described herein.

Fluorescence imaging control systems and methods are described herein. As will be described below in more detail, a fluorescence imaging control system may be configured to direct an illumination source to illuminate a scene with fluorescence excitation illumination configured to excite one or more fluorophores present at the scene and direct an imaging device to detect fluorescence emitted by the fluorophore(s) in response to excitation of the fluorophore(s) by the fluorescence excitation illumination. The fluorescence imaging control system may further be configured to determine, based on the detected fluorescence, a lifetime of the fluorescence. Based on the determined lifetime of the fluorescence, the fluorescence imaging control system may determine an identity of the fluorophore or identify a type of tissue or regions of different tissue types in which the fluorophore is present.

As used herein, "fluorescence lifetime" (also referred to herein simply as "lifetime") may refer to an amount (e.g., an average amount) of time a fluorophore molecule spends in an excited state before returning to a ground state by emitting a photon. When a molecule of a fluorophore absorbs a photon of appropriate energy (e.g., fluorescence excitation illumination having a particular wavelength), the molecule transitions to an excited state. The excited fluorophore molecule then returns to the ground state through a series of decay processes, one of which includes a spontaneous emission of a photon that occurs at a decay rate of k. The fluorescence lifetime $\tau$ is reciprocally proportional to the decay rate k ($\tau=1/k$). If a population of fluorophores is excited, the fluorescence lifetime can also be shown to be the time it takes for N excited molecules to be reduced by a factor of e. That is, the fluorescence lifetime is the time required by N excited molecules to decrease exponentially to N/e (~36.8%) of the original population. Assuming that an intensity of the fluorescence is related to the population of fluorophores returning to the ground state, the fluorescence will decay with time according to the following Equation [1]:

$$I(t)=I_0 e^{-t/\tau} \quad [1]$$

where t is time, $\tau$ is the fluorescence lifetime of the fluorescence, $I_0$ is the initial intensity of the fluorescence at t=0, and I(t) is the intensity at time t.

In some examples, the fluorescence imaging control system may be configured to perform one or more operations based on the determined identity of a fluorophore. For example, the fluorescence imaging control system may set a configuration of the fluorescence excitation illumination (e.g., a wavelength or wavelength band, a waveform, an intensity, a frequency, a pulse-width, a period, a modulation, etc.) and/or a configuration of the imaging device (e.g., a sampling rate, an exposure time, a gain, an activation timing, etc.) based on the determined identity of the fluorophore (e.g., based on an optical property of the identified fluorophore). Additionally or alternatively, the fluorescence imaging control system may configure, based on the identity of the fluorophore, display of an image (e.g., a fluorescence image, an augmented image, etc.) generated based on the detected fluorescence. These and other operations that may be performed by the fluorescence imaging control system based on the determined identity of the fluorophore are described herein.

In additional examples, the fluorescence imaging control system may be configured to perform one or more operations based on the determined type of tissue in which the fluorophore is present. For example, the fluorescence imaging control system may set a configuration of the fluorescence excitation illumination and/or a configuration of the imaging device based on the determined type of tissue in which the fluorophore is present. Additionally or alternatively, the fluorescence imaging control system may configure, based on the type of tissue in which the fluorophore is present, display of an image (e.g., a fluorescence image, an augmented image, etc.) generated based on the detected fluorescence. These and other operations that may be performed by the fluorescence imaging control system based on the determined type of tissue in which the fluorophore is present are described herein.

The systems and methods described herein may provide various benefits. For example, the systems and methods described herein may automatically determine an identity of a fluorophore present in patient tissue without requiring user input indicating the identity of the fluorophore. In particular, the systems and methods described herein may be configured to identify the fluorophore based on a measured lifetime of the detected fluorescence. This may advantageously result in substantially real-time determination of the identity and concentration of a fluorophore present in patient tissue. Additionally, determination of fluorescence lifetime emitted by a fluorophore from different tissue types may enable surgical scene segmentation, delineating critical tissues such as, but not limited to, nerves, vasculature, and healthy versus diseased (e.g., cancerous) tissue.

Additionally, the systems and methods described herein may automatically optimize, based on the identity of the fluorophore or the tissue type in which the fluorophore is present, operation of a fluorescence imaging system (e.g., a fluorescence excitation illumination source and/or a fluorescence imaging device) used during a surgical procedure, thereby improving a quality of a fluorescence image generated by the fluorescence imaging system. The systems and methods described herein may also automatically optimize, based on the identity of the fluorophore or the tissue type in which the fluorophore is present, the display of a fluorescence image based on the detected fluorescence. Each of these operations may improve efficiency and effectiveness of a surgical procedure. These and other benefits of the systems and methods described herein will be made apparent in the description that follows.

FIG. 1 illustrates a functional diagram of an exemplary imaging system 100 that may be used in accordance with the systems and methods described herein to capture visible light images of a scene (e.g., a surgical area associated with a patient) and fluorescence images of the scene. As shown, imaging system 100 includes an imaging device 102 and a controller 104. Imaging system 100 may include additional or alternative components as may serve a particular implementation. For example, imaging system 100 may include various optical and/or electrical signal transmission components (e.g., wires, lenses, optical fibers, choke circuits, waveguides, etc.), a cable that houses electrical wires and/or optical fibers and that is configured to interconnect imaging device 102 and controller 104, etc. While imaging system 100 shown and described herein comprises a fluorescence imaging system integrated with a visible light imaging system, imaging system 100 may alternatively be implemented as a standalone fluorescence imaging system configured to capture only fluorescence images of the scene. Accordingly, components of imaging system 100 that function only to capture visible light (e.g., white light) images may be omitted. In some examples a standalone fluorescence imaging system may be physically integrated with a visible light imaging system, such as by inserting the fluorescence imaging system into an assistance port of an endoscope.

As shown in FIG. 1, imaging device 102 may be used to capture visible light images and fluorescence images of a scene. An exemplary scene includes patient tissue 106 and a fluorophore 108 present within tissue 106. The scene may also include other objects not shown in FIG. 1, such as a surgical instrument. Fluorophore 108 may be any suitable fluorophore configured to emit fluorescence upon excitation by fluorescence excitation illumination. Suitable fluorophores may include, for example, endogenous compounds (e.g., flavin adenine dinucleotide (FAD), reduced nicotinamide adenine dinucleotide (NADH), riboflavin, collagen, etc.) as well as exogenous compounds, organic dyes, proteins, quantum dots, organometallic complexes, lanthanides, fullerenes, nanotubes, and the like. Fluorophore 108, when used in the singular, refers to a particular type of fluorophore (e.g., indocyanine green (ICG), fluorescein, rhodamine, etc.) present in the scene, whether as a single molecule or a population of molecules. As will be explained in more detail, imaging device 102 may capture visible light images of tissue 106 and/or other objects within the scene based on visible light 110 reflected by tissue 106 and other objects at the scene, and may capture fluorescence images based on fluorescence 112 emitted by fluorophore 108.

Imaging device 102 may be implemented by any suitable device configured to capture images of a scene. In some examples, as shown in FIG. 1, imaging device 102 is implemented by an endoscope. Imaging device 102 includes a camera head 114, a shaft 116 coupled to and extending away from camera head 114, image sensors 118 (e.g., a visible light sensor 118-V and a fluorescence detection sensor 118-F), and an illumination channel 120, Imaging device 102 may be manually handled and controlled (e.g., by a surgeon performing a surgical procedure on a patient). Alternatively, camera head 114 may be coupled to a manipulator arm of a computer-assisted surgical system and controlled using robotic and/or teleoperation technology. The distal end of shaft 116 may be positioned at or near the scene that is to be imaged by imaging device 102. For example, the distal end of shaft 116 may be inserted into a patient.

Visible light sensor 118-V is configured to detect (e.g., capture, collect, sense, or otherwise acquire) visible light 110 reflected from tissue 106 and any objects included within the scene, such as surgical instruments. As will be explained below, visible light sensor 118-V may convert the detected visible light into data representative of one or more visible light images.

Visible light sensor 118-V may be implemented by any suitable image sensor, such as a charge coupled device ("CCD") image sensor, a complementary metal-oxide semiconductor ("CMOS") image sensor, or the like. In some examples, as shown in FIG. 1, visible light sensor 118-V is positioned at the distal end of shaft 116. Alternatively, visible light sensor 118-V may be positioned closer to a proximal end of shaft 116, inside camera head 114, or outside imaging device 102 (e.g., inside controller 104). In these alternative configurations, optics (e.g., lenses, optical fibers, etc.) included in shaft 116 and/or camera head 114 may convey light from the scene to visible light sensor 118-V.

Fluorescence detection sensor 118-F is configured to detect (e.g., capture, collect, sense, or otherwise acquire) fluorescence 112 emitted by fluorophore 108. Fluorescence 112 may have a wavelength in an ultraviolet, visible, and/or infrared region. As will be explained below, fluorescence detection sensor 118-F may convert the detected fluorescence 112 into data representative of one or more fluorescence images.

Fluorescence detection sensor 118-F may be implemented by any suitable sensor configured to detect fluorescence 112 and enable determination of a lifetime of the detected fluorescence 112. As will be explained below, the lifetime of the detected fluorescence may be determined, for example, according to a time-domain technique, a frequency-domain technique, or any other suitable technique. Accordingly, in some embodiments fluorescence detection sensor 118-F may be implemented by any suitable sensor configured for time-domain and/or frequency-domain determination of the fluorescence lifetime. Suitable sensors include, without limitation, photodetectors based on time-correlated single photon counting (TCSPC) (e.g., a single photon counting detector, a photo multiplier tube (PMT), a single photon avalanche diode (SPAD) detector, etc.), photodetectors based on time-gating (e.g., intensified CCDs), time-of-flight sensors, streak cameras, and the like.

In alternative embodiments, fluorescence detection sensor 118-F may be implemented by a plurality of image sensors, such as CCD image sensors and/or CMOS image sensors, each configured to sample fluorescence at a different timing. As will be explained below, such sensors often alone sample too slowly to enable determination of a fluorescence lifetime (which often occurs on the order of nanoseconds). However, a plurality of such sensors may be uniquely configured to operate in succession to collect sufficient fluorescence image signals to enable determination of the fluorescence lifetime. Alternatively to a plurality of distinct image sensors, fluorescence detection sensor 118-F may instead be implemented by a single sensor having a plurality of distinct regions that sample fluorescence in succession to collect sufficient fluorescence image signals to enable determination of the fluorescence lifetime. Exemplary multi-sensor and multi-region sensor configurations will be described below in more detail.

In some embodiments, fluorescence detection sensor 118-F may be implemented by a plurality of distinct sensors (or regions on a single sensor) each tailored for a particular purpose, e.g., a distinct wavelength of fluorescence. For instance, a first fluorescence detection sensor may include a first filter configured to enable detection of fluorescence in a first wavelength band (e.g., a near-infrared band), a second fluorescence detection sensor may include a second filter configured to enable detection of fluorescence in a second wavelength band (e.g., an ultraviolet band), and a third fluorescence detection sensor may include a third filter configured to enable detection of fluorescence in a third wavelength band (e.g., a visible light band). In additional or alternative examples, each sensor (or region of a sensor) may be configured to operate with a different sampling rate, imaging parameters (e.g., exposure, gain, etc.), and the like.

Fluorescence detection sensor 118-F may be positioned at the distal end of shaft 116, or it may alternatively be positioned closer to the proximal end of shaft 116, inside camera head 114, or outside imaging device 102 (e.g., inside controller 104). In these alternative configurations, optics included in shaft 116 and/or camera head 114 may convey fluorescence 112 from the scene to fluorescence detection sensor 118-F. In some examples, fluorescence detection sensor 118-F may share optics with visible light sensor 118-V.

Fluorescence detection sensor 118-F may capture images of all or part of the scene captured by visible light sensor 118-V. In some examples the field of view of fluorescence detection sensor 118-F may be the same as visible light sensor 118-V but may differ slightly (due to its position within shaft 116) without loss of utility.

In some examples imaging device 102 is stereoscopic, in which case visible light sensor 118-V includes two sensors configured to capture left and right visible images of the scene. Likewise, fluorescence detection sensor 118-F may include two distinct sensors configured to capture left and right fluorescence images of the scene. In other examples imaging device 102 is monoscopic, in which case visible light sensor 118-V and/or fluorescence detection sensor 118-F are configured to capture a single visible light image and a single fluorescence image, respectively.

Image sensors 118 may be configured to operate in accordance with one or more definable (e.g., adjustable) parameters (e.g., activation times/sampling rate, exposure period, auto exposure, gain, etc.).

Illumination channel 120 may be implemented by one or more optical components (e.g., optical fibers, light guides, lenses, etc.). As will be described below, illumination may be provided to the scene by way of illumination channel 120 to illuminate the scene.

Controller 104 may be implemented by any suitable combination of hardware and software configured to control and/or interface with imaging device 102. For example, controller 104 may be at least partially implemented by a computing device included in a computer-assisted surgical system.

Controller 104 includes a camera control unit ("CCU") 122 and illumination sources 124 (e.g., a visible light illumination source 124-V and a fluorescence excitation illumination source 124-F). Controller 104 may include additional or alternative components as may serve a particular implementation. For example, controller 104 may include circuitry configured to provide power to components included in imaging device 102. In some examples, CCU 122 and/or illumination sources 124 are alternatively included in imaging device 102 (e.g., in camera head 114).

CCU 122 may be configured to control (e.g., define, adjust, configure, set, etc.) any of the definable parameters of image sensors 118. CCU 122 may also be configured to receive and process image data from image sensors 118. While CCU 122 is shown in FIG. 1 to be a single unit, CCU 122 may alternatively be implemented by multiple CCUs each configured to control distinct image streams (e.g., a visible light image stream, a fluorescence image stream, a right-side fluorescence image stream, a left-side image fluorescence stream, etc.).

Illumination sources 124 may be configured to generate and emit illumination 126. Illumination 126 (which may also be referred herein to as light) may travel by way of illumination channel 120 to a distal end of shaft 116, where illumination 126 exits to illuminate the scene. Illumination 126 generated by visible light illumination source 124-V may include visible light 126-V having one or more color components or a continuous spectrum of light (e.g., white light). Illumination generated by fluorescence excitation illumination source 124-F may include fluorescence excitation illumination 126-F configured to excite fluorophore 108. Fluorescence excitation illumination 126-F may include one or more broadband spectra of light or may include one or more discrete wavelengths of light.

Illumination sources 124 may be configured to operate in accordance with one or more definable (e.g., adjustable) parameters (e.g., parameters that specify a wavelength or wavelength band, a waveform, an intensity, a frequency, a pulse-width, a period, a modulation, etc.). Illumination sources 124 may be implemented by any suitable device, such as a flash lamp, laser source, laser diode, light-emitting diode, and the like. While each illumination source 124 is shown to be a single device in controller 104, each illumination source 124 may alternatively include multiple illumination sources each configured to generate and emit differently configured illumination. Alternatively, while illumination sources 124 are shown in FIG. 1 to be multiple units, illumination sources 124 may instead be implemented by a single unit configured to emit both visible light 126-V and fluorescence excitation illumination 126-F.

To capture one or more images of a scene, controller 104 (or any other suitable computing device) may activate illumination sources 124 and image sensors 118. While activated, illumination sources 124 concurrently emit illumination 126, which travels via illumination channel 120 to the scene, Visible light sensor 118-V detects visible light 110 (e.g., the portion of visible light 126-V that is reflected from one or more surfaces in the scene, such as tissue 106), and fluorescence detection sensor 118-F detects fluorescence 112 that is emitted by fluorophore 108 upon excitation by fluorescence excitation illumination 126-F.

Visible light sensor 118-V (and/or other circuitry included in imaging device 102) may convert the detected visible light 110 into visible light image data 128-V representative of one or more visible light images of the scene. Similarly, fluorescence detection sensor 118-F (and/or other circuitry included in imaging device 102) may convert the detected fluorescence 112 into fluorescence image data 128-F representative of one or more fluorescence images of the scene. Image data 128 (e.g., visible light image data 128-V and fluorescence image data 128-F) may have any suitable format.

Image data 128 is transmitted from image sensors 118 to CCU 122. Image data 128 may be transmitted by way of any suitable communication link between image sensors 118 and CCU 122. For example, image data 128 may be transmitted by way of wires included in a cable that interconnects imaging device 102 and controller 104. Additionally or alternatively, image data 128 may be transmitted by way of one or more optical fibers.

CCU 122 may process (e.g., packetize and/or format) image data 128 and output processed image data 130 (e.g., processed visible light image data 130-V corresponding to visible light image data 128-V and processed fluorescence image data 130-F corresponding to fluorescence image data 128-F). CCU 122 may transmit processed image data 130 to an image processor (not shown) for further processing.

The image processor may be implemented by one or more computing devices external to imaging system 100, such as one or more computing devices included in a computer-assisted surgical system. Alternatively, the image processor may be included in controller 104. The image processor may prepare processed image data 130 for display by one or more display devices (e.g., in the form of one or more still images and/or video content). For example, the image processor may generate, based on processed visible light image data 130-V, a plurality of visible light images, which may be sequentially output to form a visible light image stream. The visible light images may include full color images and/or grayscale images. The image processor may also generate, based on processed fluorescence image data 130-F, a plurality of fluorescence images, which may be sequentially output to form a fluorescence image stream. System 100 may direct one or more display devices to then display the visible light image stream and/or the fluorescence image stream.

In some examples the image processor may combine (e.g., blend) processed visible light image data 130-V and processed fluorescence image data 130-F to generate a plurality of augmented images, which may be sequentially output to form an augmented image stream for display by one or more display devices. An augmented image may display fluorescing regions (derived from processed fluorescence image data 130-F) artificially colored, such as green or blue, to highlight the fluorescing regions. Additionally, the image processor may be configured to selectively apply a gain to a fluorescence image to adjust (e.g., increase or decrease) the illumination intensity of the fluorescing regions. System 100 may direct one or more display devices to display the augmented image stream.

In some examples, the image processor may operate in accordance with one or more definable (e.g., adjustable) parameters. As will be explained below in more detail, the image processor may be configured to set a color of fluorescing regions, perform white balance, correct processed image data 130, and perform other similar operations based on the determined identity of fluorophore 108 or based on the type of tissue 106 in which fluorophore 108 is present.

In some examples, imaging system 100 is connected to, integrated into, or implemented by a surgical system. For example, imaging system 100 may be connected to, integrated into, or implemented by a computer-assisted surgical system that utilizes robotic and/or teleoperation technology to perform a surgical procedure (e.g., a minimally invasive surgical procedure). An exemplary computer-assisted surgical system is described herein.

In some scenarios an identity of fluorophore 108 present in tissue 106 may be unknown to imaging system 100. As a result, operation of imaging system 100 may not be optimally configured for capture of fluorescence images, and captured fluorescence images may not be optimally configured for display by a display device. In other scenarios, an identity of fluorophore 108 present in tissue 106 may be known, but the type of tissue 106 in which fluorophore 108 is present is unknown. Therefore, fluorescence images based on fluorescence 112 may not convey useful information about tissue 106 in which fluorophore 108 is present.

To address these problems, a fluorescence imaging control system may be configured to determine a fluorescence lifetime of fluorescence 112. Based on the determined fluorescence lifetime, the fluorescence imaging control system may determine an identity of fluorophore 108 or a type of tissue 106 in which fluorophore 108 is present. The fluorescence imaging control system may also be configured to control operation of imaging system 100 and/or an image processor based on the determined identity of fluorophore 108 or the type of tissue 106 in which fluorophore 108 is present.

Figure 2:
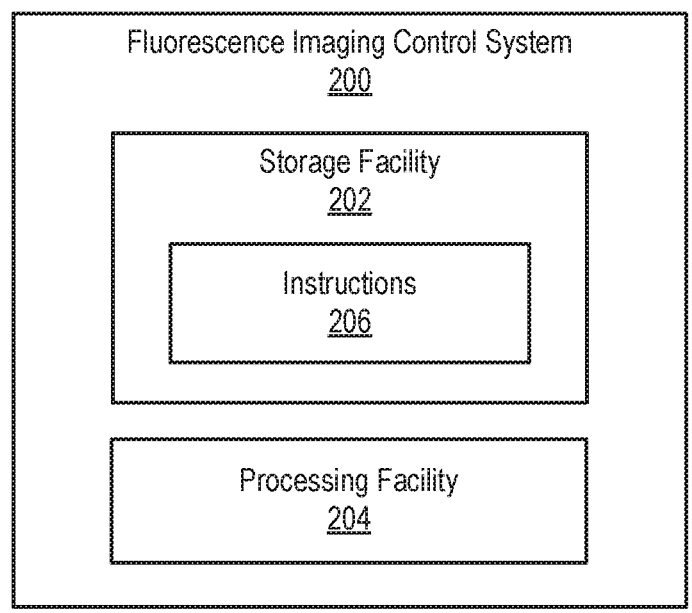
FIG. 2 illustrates an exemplary fluorescence imaging control system according to principles described herein.

FIG. 2 illustrates an exemplary fluorescence imaging control system 200 ("system 200") that may be configured to determine an identity of a fluorophore present at a scene or a type of tissue in which the fluorophore is present and/or identify distinct regions of different tissue types in which the fluorophore is present. System 200 may be included in, implemented by, or connected to any surgical systems or other computing systems described herein. For example, system 200 may be implemented by a computer-assisted surgical system. As another example, system 200 may be implemented by a stand-alone computing system communicatively coupled to a computer-assisted surgical system.

As shown, system 200 includes, without limitation, a storage facility 202 and a processing facility 204 selectively and communicatively coupled to one another. Facilities 202 and 204 may each include or be implemented by hardware and/or software components (e.g., processors, memories, communication interfaces, instructions stored in memory for execution by the processors, etc.). For example, facilities 202 and 204 may be implemented by any component in a computer-assisted surgical system. In some examples, facilities 202 and 204 may be distributed between multiple devices and/or multiple locations as may serve a particular implementation.

Storage facility 202 may maintain (e.g., store) executable data used by processing facility 204 to perform any of the operations described herein. For example, storage facility 202 may store instructions 206 that may be executed by processing facility 204 to perform any of the operations described herein. Instructions 206 may be implemented by any suitable application, software, code, and/or other executable data instance. Storage facility 202 may also maintain any data received, generated, managed, used, and/or transmitted by processing facility 204.

Processing facility 204 may be configured to perform (e.g., execute instructions 206 stored in storage facility 202 to perform) various operations associated with determining an identity of a fluorophore present at a scene or identifying a type of tissue or distinct regions of different tissue types in which the fluorophore is present. For example, processing facility 204 may be configured to direct an illumination source to illuminate a scene with fluorescence excitation illumination configured to excite a fluorophore present at the scene, and direct an imaging device to detect fluorescence emitted by the fluorophore in response to the excitation of the fluorophore by the fluorescence excitation illumination. Processing facility 204 may also be configured to determine, based on the detected fluorescence, a lifetime of the fluorescence. Processing facility 204 may be configured to determine, based on the determined lifetime of the fluorescence, an identity of the fluorophore or identify a type of tissue or distinct region in which the fluorophore is present. In some examples, processing facility 204 may be configured to perform one or more operations based on the determined identity of the fluorophore or based on the determined type of tissue in which the fluorophore is present. These and other operations that may be performed by processing facility 204 are described herein. In the description that follows, any references to operations performed by system 200 may be understood to be performed by processing facility 204 of system 200.

As mentioned, system 200 may be configured to determine a lifetime of fluorescence emitted by a fluorophore present at a scene. The lifetime may be measured or determined in any suitable way, including but not limited to by a time-domain method or a frequency-domain method.

In the time-domain method, system 200 is configured to direct an illumination source (e.g., fluorescence excitation illumination source 124-F) to illuminate a scene with short pulses of fluorescence excitation illumination (e.g., fluorescence excitation illumination 126-F) configured to excite a fluorophore (e.g., fluorophore 108) present at the scene.

Figure 3:
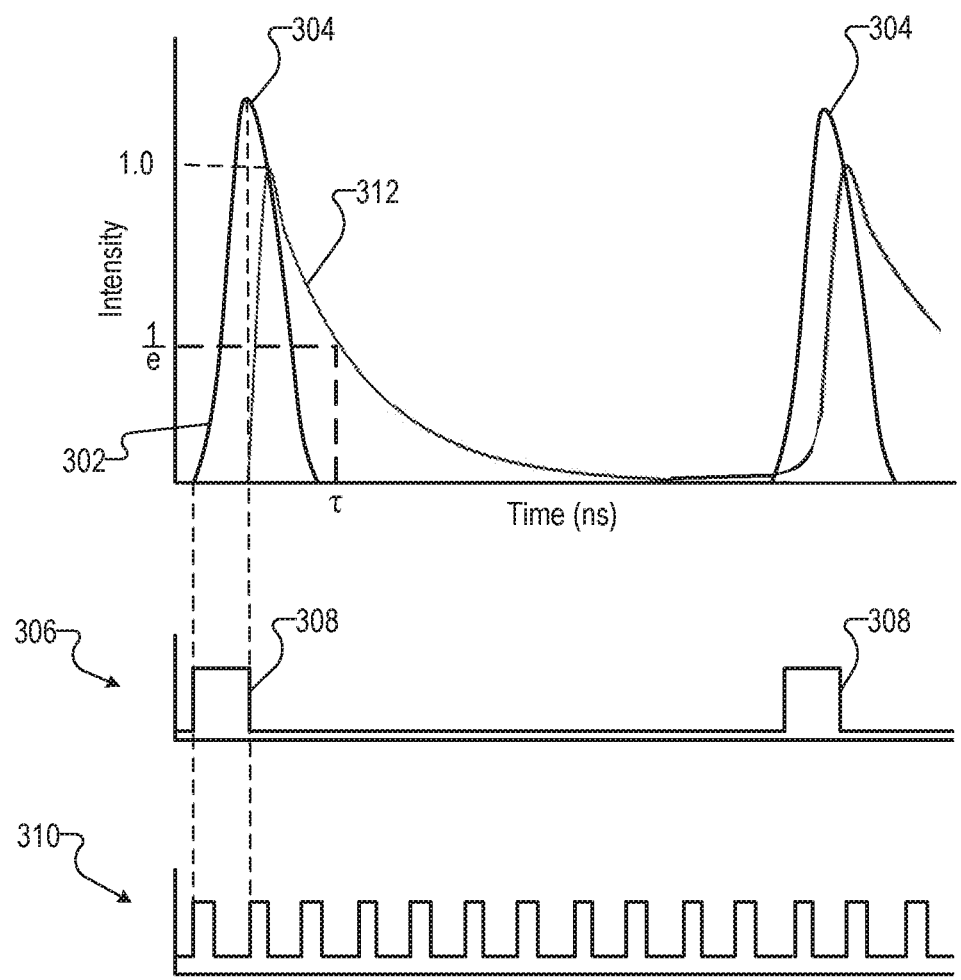
FIG. 3 illustrates an exemplary fluorescence excitation illumination curve and fluorescence decay curve and exemplary timing of emitting fluorescence excitation illumination and activating fluorescence detection according to principles described herein.

FIG. 3 shows a curve 302 representing an exemplary pulsed fluorescence excitation illumination in which time is shown on the x-axis and intensity is shown on the y-axis. As shown by curve 302, the fluorescence excitation illumination has a plurality of pulses 304. System 200 may set a pulse width and a period (or frequency) to any values as may suit a particular implementation. In some examples, the period is greater than or equal to the lifetime of fluorescence emitted by a fluorophore excited by the fluorescence excitation illumination, and the pulse width is shorter than an expected fluorescence lifetime of the fluorescence. In some examples, the pulse width is less than about 100 nanoseconds (ns). In other examples, the pulse width is less than about 10 ns. In yet other examples, the pulse width is less than about 3 ns.

System 200 may control the fluorescence excitation illumination source in any suitable manner. FIG. 3 shows an exemplary drive signal 306 configured to drive operation of the fluorescence excitation illumination source to produce the fluorescence excitation illumination represented by curve 302. As shown, drive signal 306 is a rectangular pulse wave having a plurality of pulses 308 configured to produce pulses 304 of the fluorescence excitation illumination. In some examples drive signal 306 electrically controls an ON/OFF state of the fluorescence excitation illumination source. Alternatively, drive signal 306 mechanically controls the output of fluorescence excitation illumination, such as by setting a speed of a spinning wheel that periodically allows transmission of the fluorescence excitation illumination.

System 200 is further configured to direct an imaging device (e.g., fluorescence detection sensor 118-F) to detect fluorescence emitted by the fluorophore in response to excitation of the fluorophore by the fluorescence excitation illumination (e.g., in response to excitation of the fluorophore by pulses 304 of the fluorescence excitation illumination). The imaging device measures the intensity of the emitted fluorescence over time, including after termination of the fluorescence excitation illumination (e.g., after each pulse 304). Any suitable method may be used to detect the fluorescence, including but not limited to TCSPC and fast time-gating (e.g., time-gating with multiple gates of equal width, time-gate scanning, etc.). In some examples the fluorescence detection sensor is implemented by a PMT or avalanche photodiode (e.g., a SPAD) configured to record the time-dependent distribution of emitted photons at each location (e.g., at each pixel) after one or more pulses 304 of the fluorescence excitation illumination. In alternative examples the fluorescence detection sensor is implemented by a fast time-gated image intensifier (e.g., an intensified CCD) configured to measure fluorescence intensity in a series of different time windows.

FIG. 3 shows an exemplary activation timing signal 310 for activating the imaging device to detect the fluorescence excitation illumination according to a time-gating method. As shown, activation timing signal 310 is configured to drive the imaging device to detect the fluorescence excitation illumination at multiple distinct times after termination of the fluorescence excitation illumination (e.g., after each pulse 304 of fluorescence excitation illumination) to thereby collect multiple fluorescence image signal data points representative of intensity as a function of time. As will be explained later in more detail, these data points may then be used to generate a decay curve from which the fluorescence lifetime can be determined.

Figure 4A:
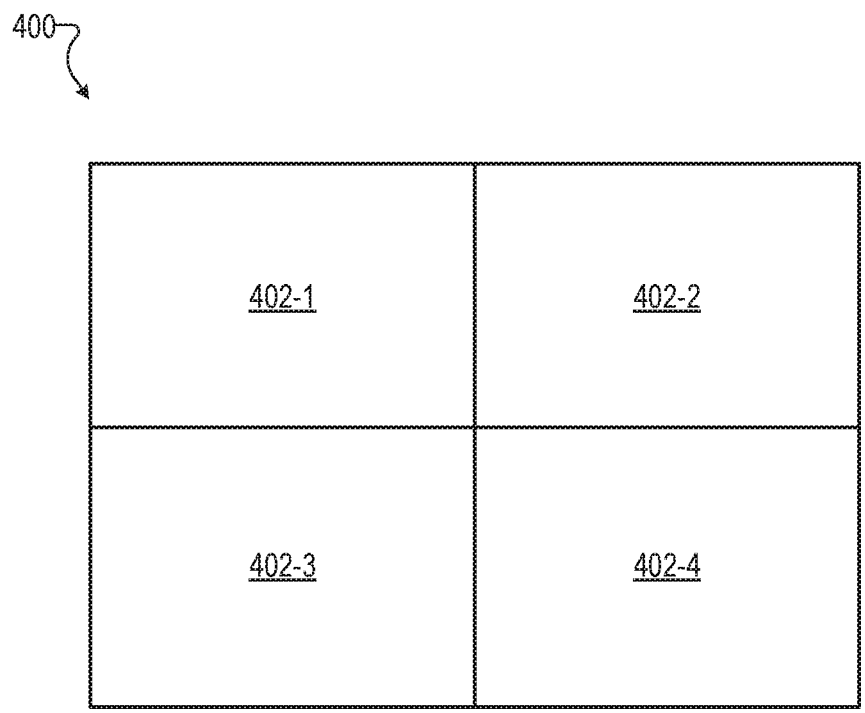
FIG. 4A illustrates an exemplary multi-region photodetector according to principles described herein.

In some examples the imaging device may be implemented by a multi-sensor and/or multi-region sensor configuration. FIG. 4A illustrates an exemplary multi-region sensor 400 configured to detect fluorescence for determination of the lifetime of the fluorescence. Sensor 400 may be implemented by any suitable sensor, such as a CCD or CMOS sensor. A sensor such as a CCD or CMOS typically does not sample light fast enough for use in determining the lifetime of detected fluorescence. To address this problem, sensor 400 is divided into a plurality of regions 402 configured to successively sample fluorescence. As shown in FIG. 4A, sensor 400 is divided into four regions (i.e., regions 402-1 through 402-4), but sensor 400 may be divided into more or fewer regions 402 as may suit a particular implementation. Each region 402 is comprised of a plurality of pixels and is configured to capture a fluorescence image of the scene. In a multi-sensor configuration, regions 402 may each be implemented by a distinct, standalone sensor.

Figure 4B:
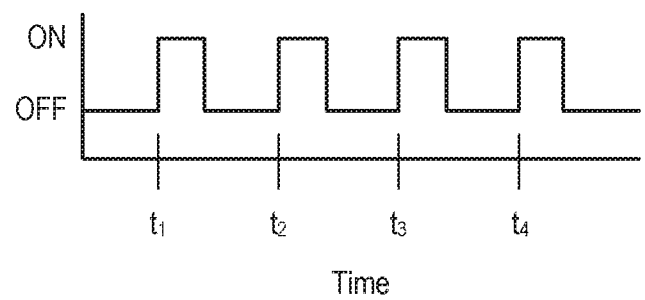
FIG. 4B illustrates an exemplary timing of activating the multi-region photodetector of FIG. 4A according to principles described herein.

Each region 402 is configured to be activated at different times in succession to generate a plurality of fluorescence images, which may then be combined to generate a decay curve from which the fluorescence lifetime can be determined, as described below in more detail. FIG. 4B illustrates an exemplary timing of activation of regions 402. At time $t_1$, region 402-1 is activated to detect fluorescence until region 402-1 is deactivated. Region 402-2 is activated at time $t_2$, region 402-3 is activated at time $t_3$, and region 402-4 is activated at time $t_4$. In this way sensor 400 is configured to generate a plurality of fluorescence image signals, with each region 402 generating a distinct fluorescence image signal. The timing between the activation of different regions 402 is set fast enough such that sensor 400 is configured to collect the plurality of fluorescence image signals during the fluorescence lifetime of the detected fluorescence. While the fluorescence lifetime is not initially known, the timing of activation of regions 402 may be estimated or initially set based on a predetermined value, and may be iteratively adjusted until sufficient data is acquired.

As mentioned, system 200 may generate a decay curve based on the fluorescence detected by the imaging device. The decay curve may be generated by any suitable method in accordance with the detection methods (e.g., TCSPC or time-gating) used. Referring again to FIG. 3, an exemplary decay curve 312 is shown. Decay curve 312 is generated based on the detected fluorescence and plots intensity of the detected fluorescence as a function of time. As can be seen, the intensity of emitted fluorescence peaks in response to pulse 304 of fluorescence excitation illumination and then decays over time according to Equation [1] described above. Fluorescence lifetime τ occurs when the value of the intensity has decayed to 1/e (~36.8%).

System 200 may be configured to determine the fluorescence lifetime T from the slope of decay curve 312 according to Equation [1]. The fluorescence lifetime T may be calculated using any suitable curve fitting algorithm, such as a least squares curve method. If the pulse width of the fluorescence excitation illumination is comparable to fluorescence lifetime T, then a deconvolution method may additionally or alternatively be used to determine fluorescence lifetime T.

As mentioned above, system 200 may alternatively determine the lifetime of the detected fluorescence by a frequency-domain method. In this method, system 200 is configured to direct the fluorescence excitation illumination source to illuminate the scene with fluorescence excitation illumination by sinusoidally modulating the fluorescence excitation illumination. As a result, the fluorescence emitted by the fluorophore is also modulated at the same frequency as the fluorescence excitation illumination but with a phase-shift and a modulation-depth (change in the amplitude) relative to the fluorescence excitation illumination.

System 200 is configured to direct the imaging device to detect the sinusoidally modulated fluorescence emitted by the fluorophore in response to excitation of the fluorophore by the fluorescence excitation illumination. The fluorescence may be detected by any sensor suitable for frequency-domain detection, such as but not limited to a PMT or CCD having a gain modulator (e.g., an intensified CCD). Any suitable method may be used to detect the phase-shift and modulation-depth from the detected fluorescence, such as a homodyne detection method. For example, the signal detected by the sensor is modulated (or gated) with the same frequency as the fluorescence excitation illumination. However, the phase of the image intensifier is shifted with respect to the fluorescence excitation illumination over time in a series of fixed steps, thereby generating a low-pass signal for each pixel. The phase-shift and modulation-depth may then be acquired from this low-pass frequency-domain signal.

System 200 is configured to determine, based on the detected fluorescence, a lifetime of the fluorescence. For example, the detected phase-shift and modulation-depth correlate to the fluorescence lifetime and the modulation frequency of the fluorescence excitation illumination according to Equation [2] and Equation [3]:

$$\omega = \tau \tan\varphi \qquad [2]$$

$$M = \frac{1}{\sqrt{(1+(\omega\tau_M)^2}} \qquad [3]$$

where $\omega$ is the modulation frequency of fluorescence excitation illumination, $\tau$ is the fluorescence lifetime of the detected fluorescence, $\varphi$ is the detected phase-shift, and M is the detected modulation-depth. Thus, the fluorescence lifetime $\tau$ can be determined in accordance with Equation [2] and/or Equation [3] by measuring the phase-shift $\varphi$ and/or modulation-depth M. The fluorescence lifetime may be determined using any suitable curve fitting algorithm, such as a least squares curve method.

The foregoing examples have described determining the fluorescence lifetime of the detected fluorescence excitation illumination according to a time-domain method or a frequency-domain method. However, system 200 is not limited to these methods, and may use any other suitable method for determining the lifetime of the fluorescence detected by the imaging device. Additionally, the foregoing examples have described illuminating the scene with pulsed fluorescence excitation illumination. However, the fluorescence excitation illumination need not be pulsed, but may have any other configuration as may suit a particular implementation. In some configurations in which the fluorescence excitation illumination is continuous, the fluorescence lifetime may be determined by suspending illumination of the scene with the fluorescence excitation illumination while the imaging device detects the fluorescence decay. The illumination may be suspended any number of times and at any timing (e.g., at regular intervals, randomly, in response to particular events, etc.) as may suit a particular implementation.

As mentioned above, in scenarios where the identity of the fluorophore present at the scene is unknown, system 200 may be configured to determine, based on the determined lifetime of the detected fluorescence (whether determined by the time-domain method, the frequency-domain method, or any other method), an identity of the fluorophore present at the scene, System 200 may determine the identity of the fluorophore in any suitable way.

In some examples, system 200 may determine the identity of the fluorophore by accessing a fluorophore lookup table comprising fluorophore data representative of a fluorescence lifetime of fluorescence emitted by each of a plurality of fluorophores. For example, the fluorophore look up table may list a plurality of fluorophores and the fluorescence lifetime for each fluorophore. In some examples the fluorescence lifetime for each fluorophore may be derived empirically. System 200 may select, from among the plurality of fluorophores, a particular fluorophore having a fluorescence lifetime that best matches the determined lifetime of the fluorescence emitted by the fluorophore present at the scene. To illustrate, system 200 may determine that the fluorescence lifetime of the detected fluorescence 112 is 4.0 ns. Accordingly, system 200 may access the fluorophore lookup table and determine that the fluorescence lifetime of fluorophore 108 best matches the fluorescence lifetime of fluorescein because fluorescein also has a fluorescence lifetime of 4.0 ns.

In some examples the fluorophore data included in the fluorophore lookup table may also include information of other fluorophore characteristics to aid in identifying the fluorophore. Such information may include, without limitation, optical properties such as information indicating a peak fluorescence excitation illumination wavelength, a peak fluorescence emission wavelength, fluorescence intensity under illumination with varying excitation illumination sources, fluorescence peak wavelength and peak shifting in various solvents or biological fluids (e.g., a solvent in which the fluorophore is present for the given fluorescence lifetime value such as lymphatic fluid, blood, etc.), a tissue type (e.g., a type of tissue and/or disease state of tissue in which the fluorophore is present for the given fluorescence lifetime value), and the like. If the fluorophore lookup table includes multiple different fluorophores with the same fluorescence lifetime, then the identity of the fluorophore present at the scene can be identified based on one or more additional characteristics. For instance, the wavelength of the fluorescence excitation illumination at the time when the fluorescence is detected by the imaging device may be used to select, from among multiple fluorophores in the fluorophore lookup table, a particular fluorophore that has both a matching fluorescence lifetime and a matching peak fluorescence excitation illumination wavelength.

In some examples, there may be more than one fluorophore present at the scene. For example, multiple fluorophores may be administered to a patient, each configured to convey different information. The principles described herein allow system 200 to determine an identity of multiple fluorophores present at the scene. For example, system 200 may be configured to direct the illumination source to illuminate the scene with fluorescence excitation illumination configured to excite a first fluorophore and a second fluorophore present at the scene. For instance, the fluorescence excitation illumination may comprise varied wavelengths (e.g., illumination in an infrared band (e.g., ranging from about 760 nm to about 1000 nm), an ultraviolet band (e.g., ranging from about 280 nm to about 380 nm), or a visible light band (e.g., ranging from about 380 nm to about 760 nm)). In this way the fluorescence excitation illumination may be configured to excite both the first fluorophore and the second fluorophore even if they have different peak fluorescence excitation illumination wavelengths. Alternatively, system 200 may be configured to direct one or more fluorescence excitation illumination sources to illuminate the scene with multiple uniquely-configured pulse waves of fluorescence excitation illumination each configured to excite a particular fluorophore.

System 200 may further direct the imaging device to detect first fluorescence emitted by the first fluorophore and second fluorescence emitted by the second fluorophore in response to excitation of the first fluorophore and the second fluorophore by the fluorescence excitation illumination. For instance, the first fluorophore and the second fluorophore may be located at different locations at the scene. Accordingly, the imaging device may detect, at a first pixel or region of pixels of the imaging device, the first fluorescence emitted by the first fluorophore, and may detect, at a second pixel or region of pixels of the imaging device, the second fluorescence emitted by the second fluorophore. In cases where the first fluorophore and the second fluorophore are located in the same location such that the emitted fluorescence overlaps (e.g., a pixel detects a mixture of the first fluorescence and the second fluorescence), the first and second fluorescence may be separated in any suitable way. In some examples the first and second fluorescence are separated spatially with optical components (e.g., dichroic filters, mirrors, lenses, etc.) configured to direct the first and second fluorescence to fall on distinct regions of the fluorescence detection sensor (or on distinct fluorescence detection sensors). As another example, the first and second fluorescence are separated in time by sequentially pulsing multiple pulse waves of fluorescence excitation illumination and sequentially detecting the first and the second fluorescence in sync with the pulse waves of fluorescence excitation illumination.

System 200 may then determine, based on the detected first fluorescence, a lifetime of the first fluorescence, and may determine; based on the detected second fluorescence, a lifetime of the second fluorescence. The lifetimes of the first fluorescence and the second fluorescence may be determined in any of the ways described herein.

System 200 may further determine, based on the determined lifetime of the first fluorescence, an identity of the first fluorophore, and may determine, based on the determined lifetime of the second fluorescence, an identity of the second fluorophore.

While the foregoing example has described determining the identity of a first fluorophore and a second fluorophore present at the scene, system 200 may be configured to determine the identity of any number of fluorophores present at the scene. As can be seen from the preceding description, the systems and methods described herein enable the determination of the identity of multiple fluorophores present at a scene by using a single sensor and/or a single fluorescence excitation illumination source. Moreover, the systems and methods described herein do not require the use of wavelength filters to discern the fluorescence emitted from multiple different fluorophores present at the scene.

As mentioned, system 200 may be configured to control operation of one or more components of a fluorescence imaging system (e.g., an image sensor 118 and/or an illumination source 124 of imaging system 100) and/or an image processor based on the determined identity of the fluorophore.

For example, system 200 may be configured to set; based on an optical property of the identified fluorophore, a configuration of the fluorescence excitation illumination (e.g., fluorescence excitation illumination 126-F). A configuration of the fluorescence excitation illumination refers, for example, to a wavelength or wavelength band, a waveform, an intensity, a frequency, a pulse-width, a period, and a modulation of the fluorescence excitation illumination. System 200 may configure the fluorescence excitation illumination in any suitable manner. For example, system 200 may adjust an operational setting of a fluorescence excitation illumination source (e.g., fluorescence excitation illumination source 124-F) and/or a mechanical component (e.g., a filter, a lens, a spinning wheel, etc.) of the fluorescence excitation illumination source. System 200 may configure the fluorescence excitation illumination based on the determined identity of the fluorophore, for example, to optimize the emitted fluorescence for detection by the imaging device, to improve the quality of the signal detected by the imaging device, to increase the quantity and accuracy of acquired data used to determine the fluorescence lifetime, to conserve battery power, to reduce processing power, to prevent the emission of certain fluorescence, and the like.

To illustrate, system 200 may configure a wavelength or wavelength band of the fluorescence excitation illumination to include and/or focus on the peak fluorescence excitation illumination wavelength of the fluorophore present at the scene, thereby optimizing the intensity of the fluorescence for detection by the imaging device. For instance, if system 200 determines that fluorophore 108 is ICG, which has a peak fluorescence excitation illumination wavelength of about 780 nm in water, system 200 may adjust fluorescence excitation illumination 126-F to include illumination having a wavelength of about 780 nm. In some examples system 200 may also narrow the band of fluorescence excitation illumination 126-F to emit only the peak fluorescence excitation illumination necessary to excite fluorophore 108. In alternative examples, such as where the fluorescence image is not relevant or desired by a user, system 200 may adjust fluorescence excitation illumination 126-F to exclude illumination configured to excite fluorophore 108 (e.g., illumination having a wavelength of about 780 nm).

As another illustration, system 200 may configure a frequency of fluorescence excitation illumination 126-F based on the lifetime of fluorescence 112 emitted by fluorophore 108. To illustrate, if system 200 determines that fluorophore 108 is coumarin 6 and has a lifetime of 2.5 ns, system 200 may adjust a frequency of fluorescence excitation illumination 126-F. This may increase the average intensity (brightness) of the fluorescence image signal, thereby improving the quality of the fluorescence image. As another example, if system 200 determines that fluorophore 108 is pyrene and has a lifetime of 70 ns or more, system 200 may reduce the frequency of excitation illumination 126-F to decrease the number of pulses 304 (see FIG. 3), to ensure that a sufficient number of data points are collected for the fluorescence lifetime determination, thereby improving the accuracy of the fluorescence lifetime determination.

As mentioned, an image processor may be configured to generate, based on the detected fluorescence, an image (e.g., a fluorescence image or an augmented image) for presentation by a display device. System 200 may also configure, based on the determined identity, distribution, and/or concentration of the fluorophore, a manner in which the image processor processes captured images (e.g., processed images 130) for presentation by the display device. For example, system 200 may specify color(s) of fluorescing regions, an intensity (brightness) of fluorescing regions, a method of blending of fluorescence images and visible light images, image correction, white balance adjustment, and the like. To illustrate, if system 200 determines that fluorophore 108 is ICG, system 200 may direct the image processor to pseudo-color the fluorescing regions a particular color (e.g., green) and increase the intensity (brightness) of the fluorescing regions in the fluorescence image. On the other hand, if system 200 determines that fluorophore 108 is fluorescein, system 200 may direct the image processor to pseudo-color the fluorescing regions a different color (e.g., blue) and decrease the intensity of the fluorescing regions.

System 200 may also be configured to set, based on the determined identity of the fluorophore (e.g., based on an optical property of the fluorophore), a configuration of the imaging device (e.g., fluorescence detection sensor 118-F). A configuration of the imaging device refers, for example, to a sampling rate of the imaging device, an activation period of the imaging device (e.g., an exposure time), a gain applied to the detected fluorescence signal, an activation timing of the imaging device, and the like. In some examples where the imaging device is implemented by a plurality of sensors (or by a plurality of distinct regions on a sensor), a configuration of the imaging device may additionally or alternatively refer to an ON/OFF state of each sensor (or each region of the sensor). System 200 may set the configuration of the imaging device in any suitable manner. For example, system 200 may adjust an operational setting of the imaging device and/or adjust a mechanical component (e.g., a filter, a shutter, etc.) of the imaging device. System 200 may configure the imaging device based on the determined identity of the fluorophore to, for example, optimize the quality of the signal detected by the imaging device, to increase the quantity and accuracy of acquired data used to determine the fluorescence lifetime, to conserve battery power, to reduce processing power, to exclude the detection of certain fluorescence signals, and the like.

To illustrate, if system 200 determines that fluorophore 108 is a type that has a fluorescence lifetime greater than 10 ns, system 200 may direct the imaging device to decrease the sampling rate. As another illustration, if system 200 determines that fluorophore 108 is a type that has a peak fluorescence wavelength of 803 nm, system 200 may direct the imaging device to turn off (or discard signals detected by) any sensors that are not configured to detect the emitted fluorescence (e.g., sensors configured to detect ultraviolet and/or visible light).

In embodiments where system 200 determines an identity of a plurality of different fluorophores present at the scene, system 200 may be configured to control operation of one or more components of an imaging system and/or an image processor based on the determined identity of each of the plurality of fluorophores present at the scene. System 200 may control operation of the fluorescence imaging system components and/or the image processor in any way described above.

Figure 5:
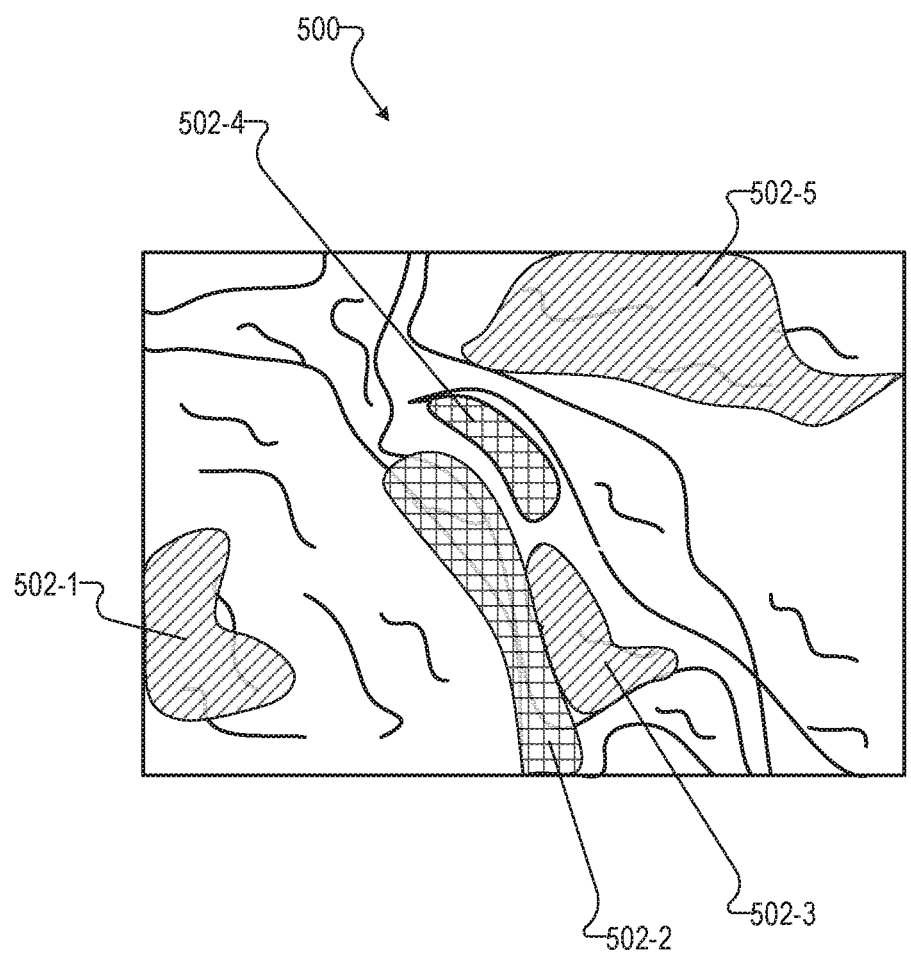
FIG. 5 illustrates an exemplary augmented medical image according to principles described herein.

For example; if system 200 determines an identity of a first fluorophore present at the scene and an identity of a second fluorophore present at the scene, as described above, system 200 may then direct the image processor to pseudo-color fluorescing regions different colors based on the determined identity of the first fluorophore and the second fluorophore. FIG. 5 illustrates an exemplary augmented image 500 in which fluorescing regions corresponding to different fluorophores are pseudo-colored differently. As shown, fluorescence image 500 includes fluorescing regions 502 (e.g., fluorescing regions 502-1 through 502-5). Fluorescing regions 502-1, 502-3, and 502-5 are generated based on fluorescence emitted by a first fluorophore ICG), and fluorescing regions 502-2 and 502-4 are generated based on fluorescence emitted by a second fluorophore (e.g., fluorescein). Accordingly, fluorescing regions 502-1, 502-3, and 502-5 are pseudo-colored a first color (e.g., green) while fluorescing regions 502-2 and 502-4 are pseudo-color a second color (e.g., blue). In this way a person viewing fluorescence image 500 may easily identify and distinguish between fluorescing regions corresponding to different fluorophores.

As mentioned above, in some scenarios an identity of a fluorophore present in tissue at the scene may be known, but the type of tissue or boundaries between regions of different types of tissue in which the fluorophore is present are unknown. Fluorescence images generated from fluorescence emitted from the fluorophore under continuous fluorescence excitation illumination may not convey useful information about the tissue in which the fluorophore is present, and fluorescence intensity in standard fluorescence imaging techniques exhibits limited changes in optical properties depending on tissue environment. However, the fluorescence lifetime of fluorescence emitted by some fluorophores may vary (significantly in some cases) depending on the type of tissue in which the fluorophore is present. Changes in fluorescence lifetimes (especially large changes) in particular tissue types relative to neighboring tissue regions enables clear delineation of tissues of interest. Accordingly, system 200 may be configured to use this characteristic to identify, based on the determined lifetime of the detected fluorescence, one or more distinct regions of different tissue types in which the fluorophore is present.

As used herein a tissue type may refer to a distinct class of tissue such as connective tissue, muscle tissue, nervous tissue, epithelial tissue, and/or any other classes of tissue such as bone tissue, a particular organ tissue (e.g., liver tissue, lung tissue, etc.), and the like. A tissue type may also refer to a condition or state of tissue such as healthy/normal, diseased, cancerous, infected, bruised, swollen, and the like.

System 200 may be configured to identify one or more distinct tissue regions in any suitable way. In some embodiments, system 200 may identify one or more distinct tissue regions by pseudo-coloring pixels of a fluorescence image based on the determined lifetime of the detected fluorescence at each pixel. For example, system 200 may generate, based on detected fluorescence emitted by a fluorophore present in a plurality of tissue types at a scene, a fluorescence image comprising a plurality of pixels. System 200 may generate the fluorescence image by determining, based on the detected fluorescence, a lifetime of the detected fluorescence at each of the plurality of pixels and pseudo-coloring the plurality of pixels based on the lifetime of the detected fluorescence at each of the plurality of pixels. Regions of a similar tissue type will thus be pseudo-colored a similar color.

Figure 6A:
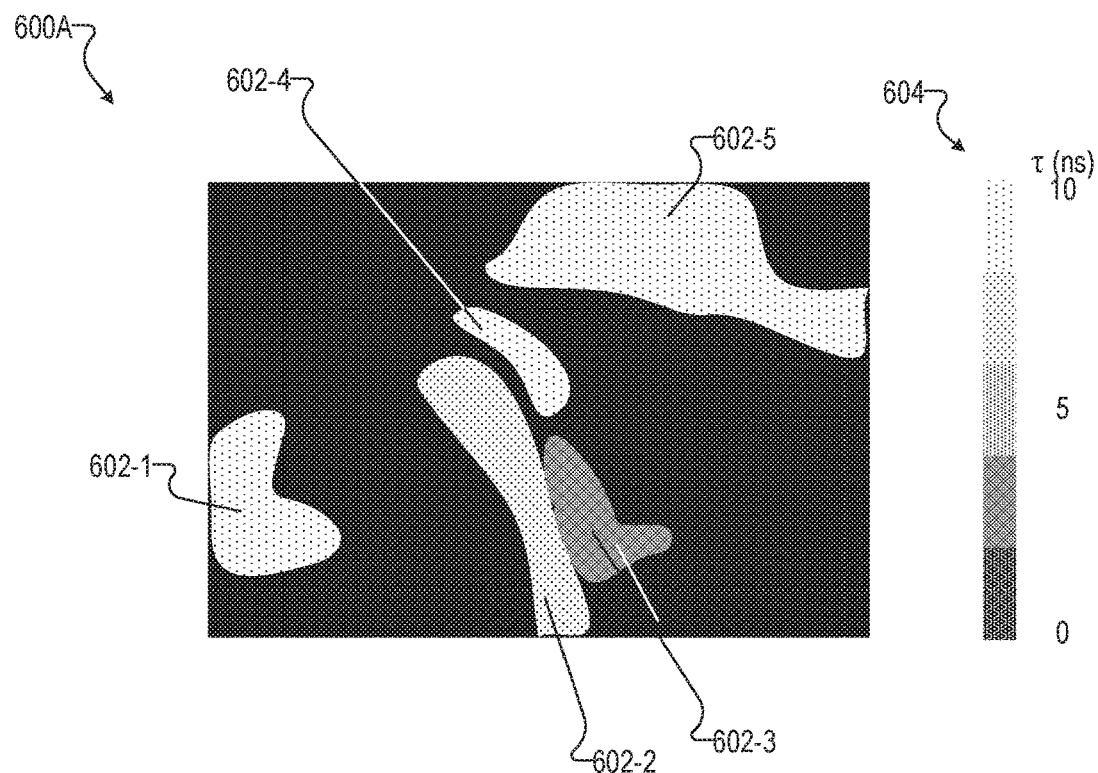
FIGS. 6A and 6B illustrate exemplary fluorescence images according to principles described herein.

FIG. 6A shows an exemplary manner of pseudo-coloring a plurality of pixels included in a fluorescence image. As shown, fluorescence image 600A includes fluorescing regions 602 (e.g., fluorescing regions 602-1 through 602-5). Fluorescing regions 602 are based on fluorescence emitted by the same type of fluorophore present at a scene (e.g., ICG). To pseudo-color fluorescing regions 602, system 200 may apply a color scale 604 that specifies colors (or shades of a color in a monochromatic image) for fluorescence lifetime values. In some examples color scale 604 is pre-configured for use with the particular fluorophore based on known fluorescence lifetime values of the fluorophore. To illustrate, a fluorophore present at a surgical area associated with a patient may be known to emit, from various different tissue types, fluorescence having a fluorescence lifetime ranging from about 0 ns up to about 10 ns. Accordingly, the color scale for the fluorophore may specify a range of visible colors ranging from, e.g., violet (at ~0 ns) to yellow (at ~5 ns) to red (at ~10 ns). Pixels that do not detect any fluorescence may be pseudo-colored, for example, black or white. Alternatively to a preconfigured color scale, system 200 may set color scale 604 based on the range of fluorescence lifetimes determined from the detected fluorescence.

As shown in FIG. 6A, pixels in fluorescing regions 602 are pseudo-colored based on the fluorescence lifetime of detected fluorescence at each pixel. For instance, the fluorescence lifetime of detected fluorescence at pixels in fluorescing regions 602-1, 602-4, and 602-5 is approximately 9 ns, so pixels in fluorescing regions 602-1, 602-4, and 602-5 are pseudo-colored a color (e.g., red) corresponding to 9 ns as specified by color scale 604. The fluorescence lifetime of detected fluorescence at pixels in fluorescing region 602-2 is approximately 5 ns, so pixels in fluorescing region 602-2 are pseudo-colored a color (e.g., yellow) corresponding to 5 ns as specified by color scale 604. The fluorescence lifetime of detected fluorescence at pixels in fluorescing region 602-3 is approximately 3 ns, so pixels in fluorescing region 602-3 are pseudo-colored a color (e.g., green) corresponding to 3 ns as specified by color scale 604.

In other examples, system 200 may pseudo-color each pixel of a fluorescence image based on a change in the measured fluorescence lifetime value of one or more adjacent pixels. For instance, system 200 may apply a color scale that specifies a particular color (or shade of a color) for a particular difference value. In some examples the difference value may be the difference between the fluorescence lifetime of a first pixel and the fluorescence lifetime of a second pixel adjacent to the first pixel in a particular direction (e.g., horizontal left-to-right, vertical top-to-bottom, etc.). In other examples the difference value may be calculated based on multiple adjacent pixels.

By pseudo-coloring a plurality of pixels in a fluorescence image based on the determined lifetime of the detected fluorescence at each of the plurality of pixels, the fluorescence image (or an augmented image based on the fluorescence image) may clearly identify regions of different tissue types. For example, a surgeon viewing image 600A may easily identify a region of cancerous tissue (e.g., fluorescing region 602-3) and regions of healthy tissue (e.g., fluorescing regions 602-1, 602-2, 602-4, and 602-5).

In some embodiments system 200 may additionally or alternatively be configured to identify the tissue type of tissue in which the fluorophore is present. In some examples, system 200 may identify the tissue type by accessing a tissue lookup table comprising tissue data representative of the fluorescence lifetime of fluorescence emitted by a particular fluorophore when present in each of a plurality of distinct tissue types. The tissue lookup table may indicate that fluorescence emitted by a particular fluorophore has a particular lifetime (e.g., 2.3 ns) when present in healthy lung tissue and has another particular lifetime (e.g., 2.7 ns) when present in cancerous lung tissue. System 200 may then select, from among the plurality of distinct tissue types, a particular tissue type in which the fluorophore has a fluorescence lifetime that best matches the determined lifetime of the detected fluorescence. To illustrate, system 200 may determine that the fluorescence lifetime of detected fluorescence 112 emitted by fluorophore 108 is 4.0 ns. System 200 may then access a tissue lookup table and determine that fluorescence 112 emitted by fluorophore 108 when present in healthy lung tissue is 3.2 ns and when in cancerous lung tissue is 4.0 ns. As a result, system 200 may determine, based on the determined lifetime of fluorescence 112, that tissue 106 in which fluorophore 108 is present is cancerous lung tissue. In some examples the fluorophore lookup table and the tissue lookup table are implemented by a single lookup table configured for fluorophore and tissue type determinations.

System 200 may be configured to control operation of one or more components of an imaging system (e.g., an image sensor 118 and/or an illumination source 124 of imaging system 100) and/or an image processor based on the determined tissue type. System 200 may be configured to control operation of components of the fluorescence imaging system and/or image processor in any of the ways described above.

Figure 6B:
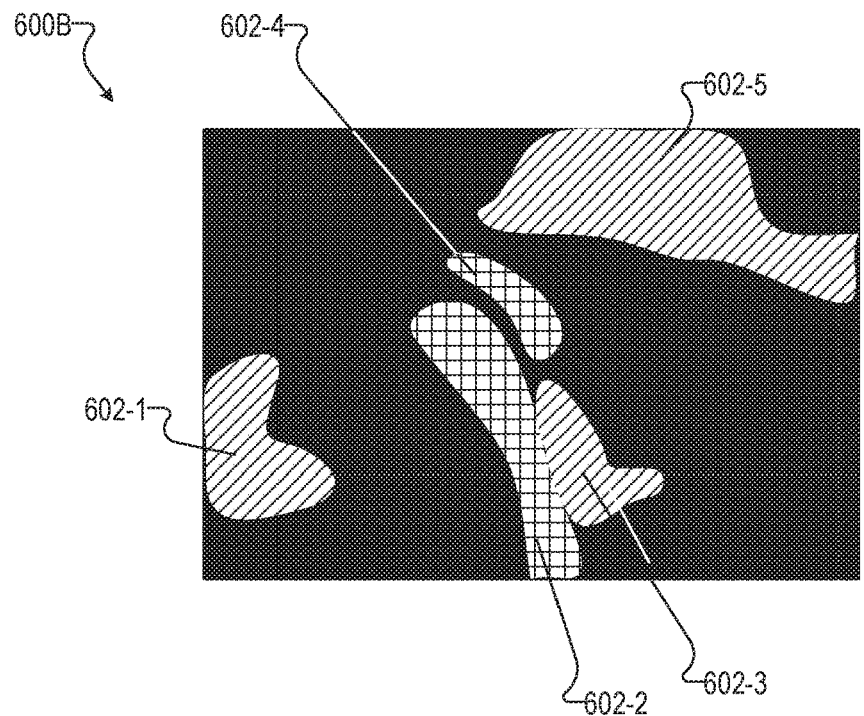

In some examples, system 200 may direct the image processor to pseudo-color fluorescing regions in a fluorescence image different colors based on the determined tissue type. FIG. 6B illustrates an exemplary manner of pseudo-coloring fluorescing regions based on the determined tissue type. FIG. 6B is similar to FIG. 6A except that fluorescing regions 602 are pseudo-colored based on the identified tissue type of each fluorescing region. Fluorescing regions 602-1, 602-3, and 602-5 are generated based on fluorescence emitted by a fluorophore from a first tissue type (e.g., healthy lung tissue) while fluorescing regions 602-2 and 602-4 are generated based on fluorescence emitted by the fluorophore from a second tissue type (e.g., cancerous lung tissue). Accordingly, fluorescing regions 602-1, 602-3, and 602-5 are pseudo-colored a first color (e.g., green) while fluorescing regions 602-2 and 602-4 are pseudo-colored a second color (e.g., red). In this way a person viewing fluorescence image 600 may easily identify and distinguish between different types of tissue (e.g., between cancerous tissue and healthy tissue) by use of a single fluorophore.

Figure 7:
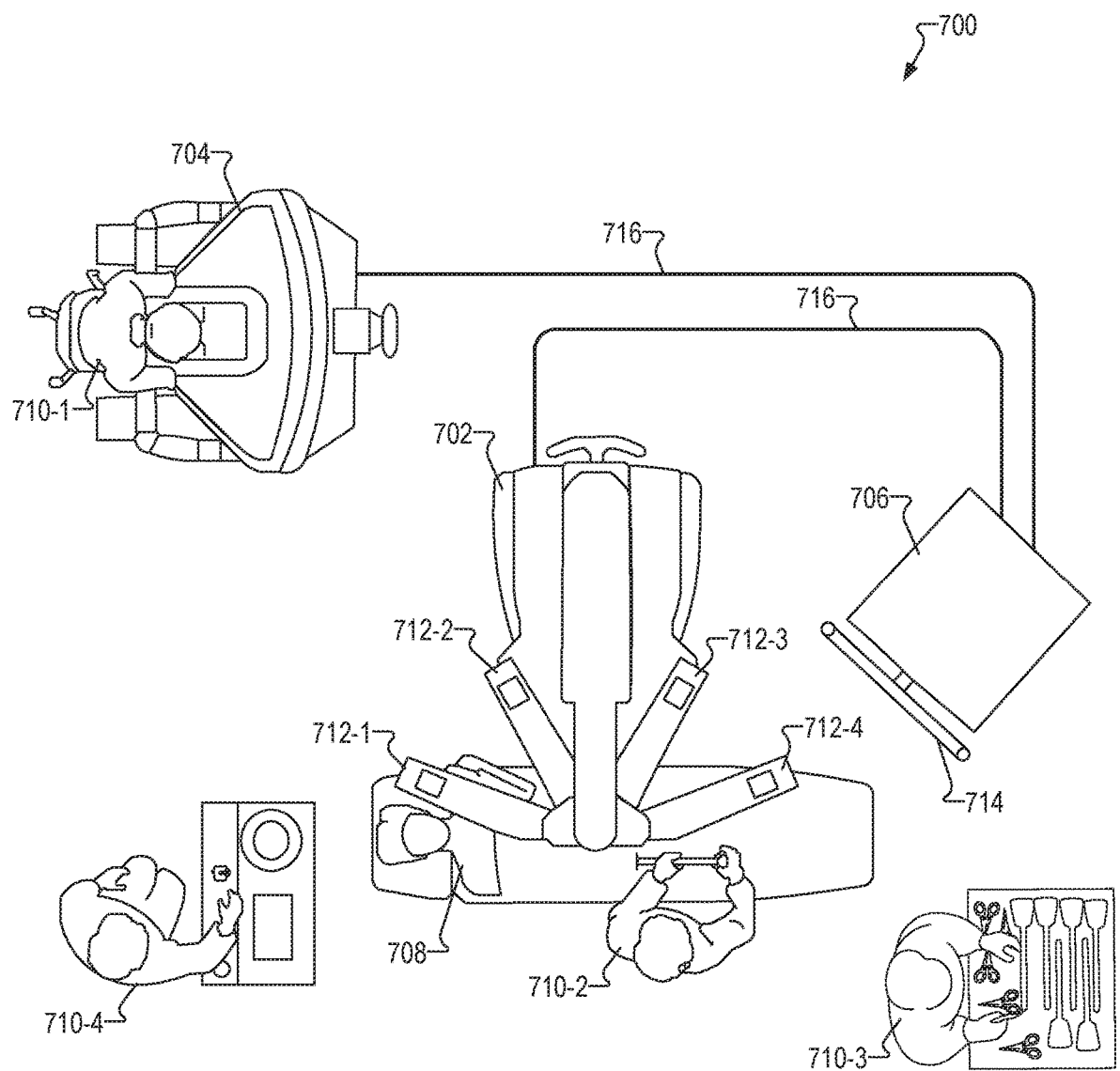
FIG. 7 illustrates an exemplary computer-assisted surgical system according to principles described herein.

FIG. 7 illustrates an exemplary computer-assisted surgical system 700 ("surgical system 700"). As described herein, system 200 may be implemented by surgical system 700, connected to surgical system 700, and/or otherwise used in conjunction with surgical system 700.

As shown, surgical system 700 may include a manipulating system 702, a user control system 704, and an auxiliary system 706 communicatively coupled one to another. Surgical system 700 may be utilized by a surgical team to perform a computer-assisted surgical procedure on a patient 708. As shown, the surgical team may include a surgeon 710-1, an assistant 710-2, a nurse 710-3, and an anesthesiologist 710-4, all of whom may be collectively referred to as "surgical team members 710." Additional or alternative surgical team members may be present during a surgical session as may serve a particular implementation.

While FIG. 7 illustrates an ongoing minimally invasive surgical procedure, it will be understood that surgical system 700 may similarly be used to perform open surgical procedures or other types of surgical procedures that may similarly benefit from the accuracy and convenience of surgical system 700. Additionally, it will be understood that the surgical session throughout which surgical system 700 may be employed may not only include an operative phase of a surgical procedure, as is illustrated in FIG. 7, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 7, manipulating system 702 may include a plurality of manipulator arms 712 (e.g., manipulator arms 712-1 through 712-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on patient 708 (e.g., by being at least partially inserted into patient 708 and manipulated to perform a computer-assisted surgical procedure on patient 708). While manipulating system 702 is depicted and described herein as including four manipulator arms 712, it will be recognized that manipulating system 702 may include only a single manipulator arm 712 or any other number of manipulator arms as may serve a particular implementation.

Manipulator arms 712 and/or surgical instruments attached to manipulator arms 712 may include one or more displacement transducers, orientational sensors, and/or positional sensors used to generate raw (i.e., uncorrected) kinematics information. One or more components of surgical system 700 may be configured to use the kinematics information to track (e.g., determine positions and orientations of) and/or control the surgical instruments.

User control system 704 may be configured to facilitate control by surgeon 710-1 of manipulator arms 712 and surgical instruments attached to manipulator arms 712. For example, surgeon 710-1 may interact with user control system 704 to remotely move or manipulate manipulator arms 712 and the surgical instruments. To this end, user control system 704 may provide surgeon 710-1 with images (e.g., high-definition 3D images, composite medical images, etc.) of a surgical area associated with patient 708 as captured by an imaging system (e.g., imaging system 100). In certain examples, user control system 704 may include a stereo viewer having two displays where stereoscopic images of a surgical area associated with patient 708 and generated by a stereoscopic imaging system may be viewed by surgeon 710-1. Surgeon 710-1 may utilize the images to perform one or more procedures with one or more surgical instruments attached to manipulator arms 712.

To facilitate control of surgical instruments, user control system 704 may include a set of master controls. These master controls may be manipulated by surgeon 710-1 to control movement of surgical instruments (e.g., by utilizing robotic and/or teleoperation technology). The master controls may be configured to detect a wide variety of hand, wrist, and finger movements by surgeon 710-1. In this manner, surgeon 710-1 may intuitively perform a procedure using one or more surgical instruments.

Auxiliary system 706 may include one or more computing devices configured to perform primary processing operations of surgical system 700. In such configurations, the one or more computing devices included in auxiliary system 706 may control and/or coordinate operations performed by various other components (e.g., manipulating system 702 and user control system 704) of surgical system 700. For example, a computing device included in user control system 704 may transmit instructions to manipulating system 702 by way of the one or more computing devices included in auxiliary system 706. As another example, auxiliary system 706 may receive, from manipulating system 702, and process image data representative of images captured by an imaging device attached to one of manipulator arms 712.

In some examples, auxiliary system 706 may be configured to present visual content to surgical team members 710 who may not have access to the images provided to surgeon 710-1 at user control system 704. To this end, auxiliary system 706 may include a display monitor 714 configured to display one or more user interfaces, such as images (e.g., 2D images, composite medical images, etc.) of the surgical area, information associated with patient 708 and/or the surgical procedure, and/or any other visual content as may serve a particular implementation. For example, display monitor 714 may display images of the surgical area together with additional content (e.g., graphical content, contextual information, etc.) concurrently displayed with the images. In some embodiments, display monitor 714 is implemented by a touchscreen display with which surgical team members 710 may interact (e.g., by way of touch gestures) to provide user input to surgical system 700.

Manipulating system 702, user control system 704, and auxiliary system 706 may be communicatively coupled one to another in any suitable manner. For example, as shown in FIG. 7, manipulating system 702, user control system 704, and auxiliary system 706 may be communicatively coupled by way of control lines 716, which may represent any wired or wireless communication link as may serve a particular implementation. To this end, manipulating system 702, user control system 704, and auxiliary system 706 may each include one or more wired or wireless communication interfaces, such as one or more local area network interfaces, Wi-Fi network interfaces, cellular interfaces, etc.

Figure 8:
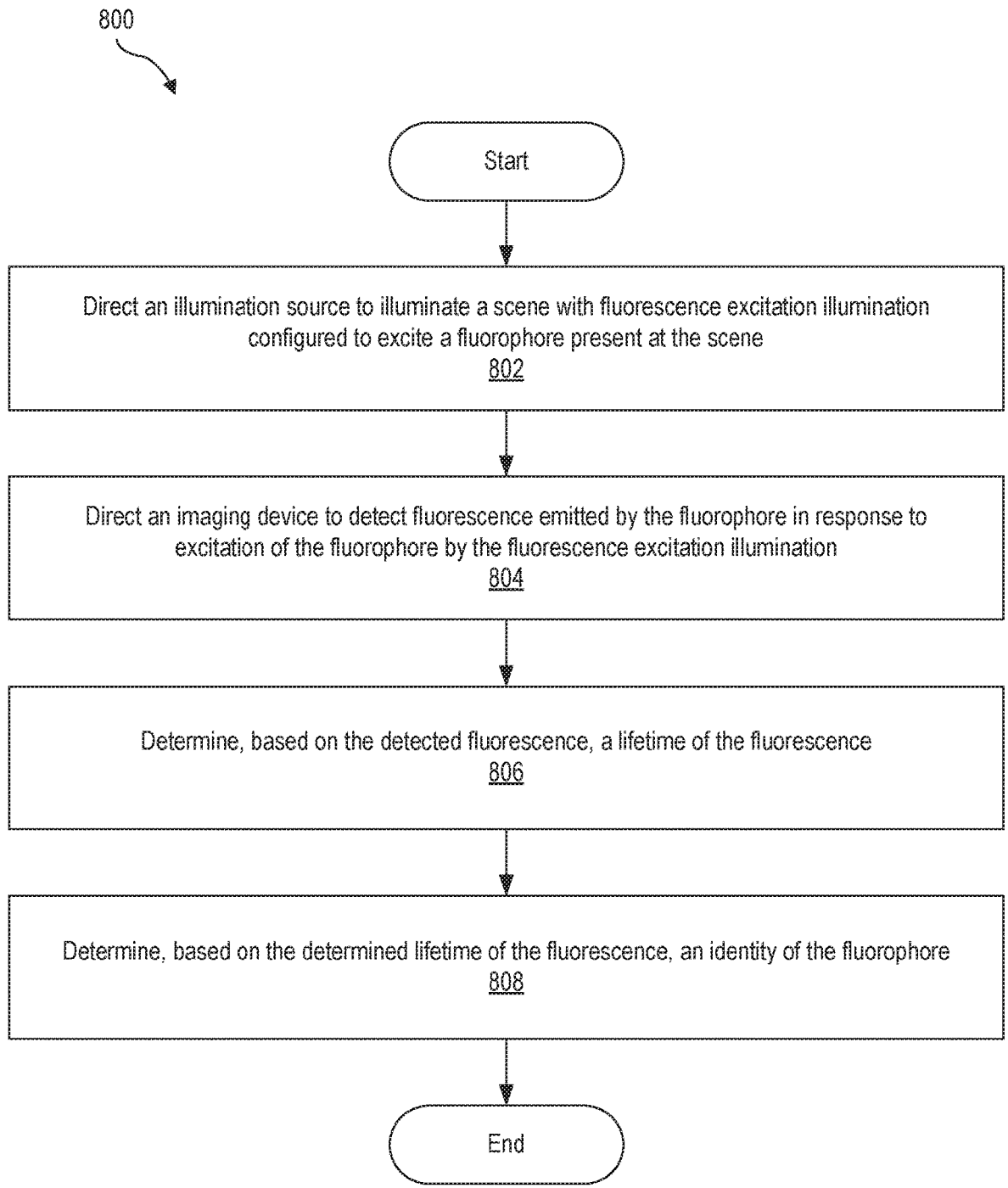
FIG. 8 illustrates an exemplary method of determining an identity of a fluorophore present at a scene according to principles described herein.

FIG. 8 shows an exemplary method 800 of determining an identity of a fluorophore present at a scene. While FIG. 8 illustrates exemplary operations according to one embodiment, other embodiments may omit, add to, reorder, combine, and/or modify any of the steps shown in FIG. 8 One or more of the operations shown in in FIG. 8 may be performed by system 200, any components included therein, and/or any implementation thereof.

In operation 802, a fluorescence imaging control system directs an illumination source to illuminate a scene with fluorescence excitation illumination configured to excite a fluorophore present at the scene. Operation 802 may be performed in any of the ways described herein.

In operation 804, the fluorescence imaging control system directs an imaging device to detect fluorescence emitted by the fluorophore in response to excitation of the fluorophore by the fluorescence excitation illumination. Operation 804 may be performed in any of the ways described herein.

In operation 806, the fluorescence imaging control system determines, based on the detected fluorescence, a lifetime of the fluorescence. Operation 806 may be performed in any of the ways described herein.

In operation 808, the fluorescence imaging control system determines, based on the determined lifetime of the fluorescence, an identity of the fluorophore. Operation 808 may be performed in any of the ways described herein.

Figure 9:
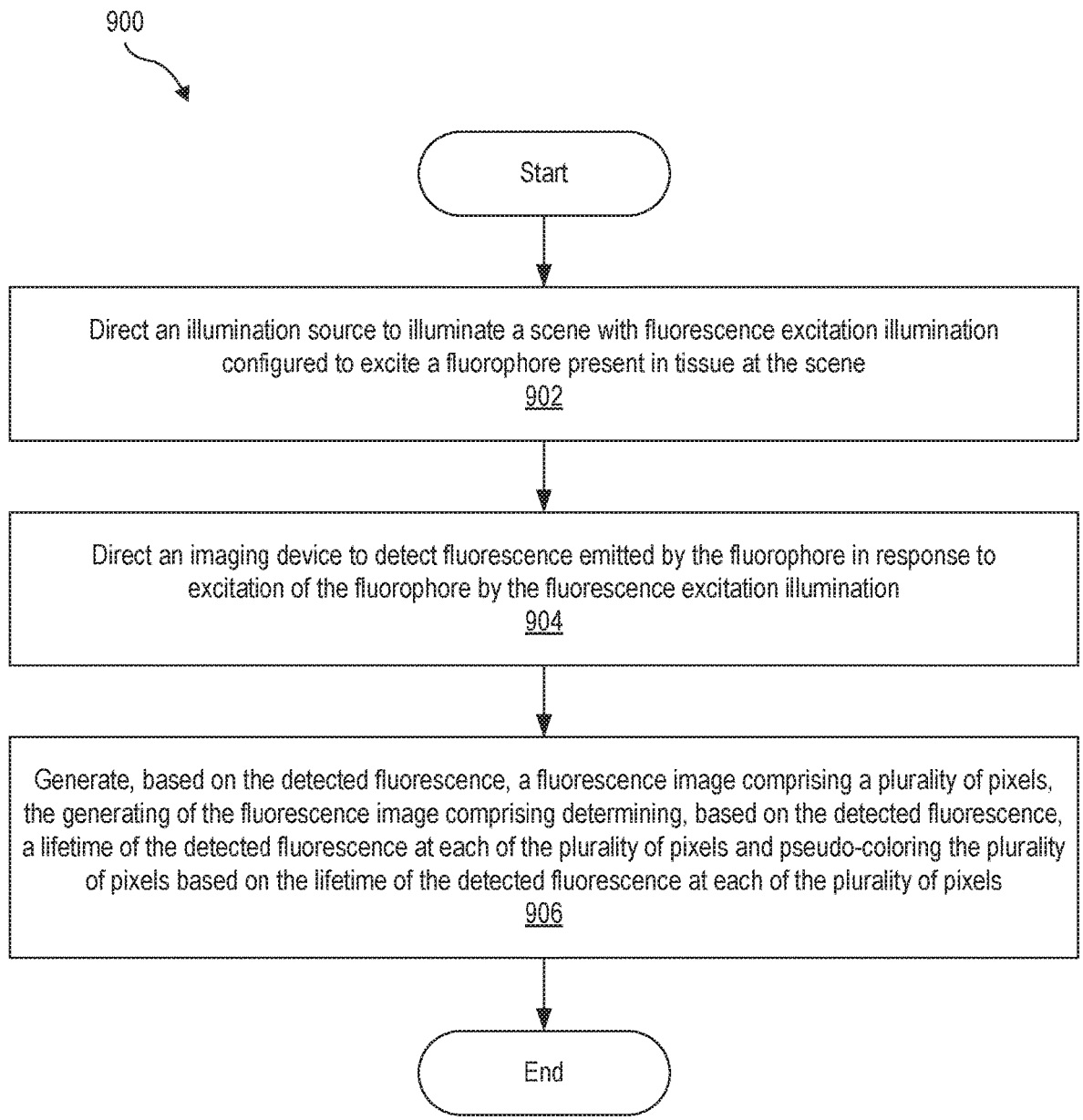
FIG. 9 illustrates an exemplary method of identifying one or more regions of distinct tissue types of tissue in which a fluorophore is present according to principles described herein.

FIG. 9 shows an exemplary method 900 of identifying one or more regions of distinct tissue types of tissue in which a fluorophore is present. While FIG. 9 illustrates exemplary operations according to one embodiment, other embodiments may omit, add to, reorder, combine, and/or modify any of the steps shown in FIG. 9 One or more of the operations shown in in FIG. 9 may be performed by system 200, any components included therein, and/or any implementation thereof.

In operation 902, a fluorescence imaging control system directs an illumination source to illuminate a scene with fluorescence excitation illumination configured to excite a fluorophore present in tissue at the scene. Operation 902 may be performed in any of the ways described herein.

In operation 904, the fluorescence imaging control system directs an imaging device to detect fluorescence emitted by the fluorophore in response to excitation of the fluorophore by the fluorescence excitation illumination. Operation 904 may be performed in any of the ways described herein.

In operation 906, the fluorescence imaging control system generates, based on the detected fluorescence, a fluorescence image comprising a plurality of pixels. The generating of the fluorescence image includes determining, based on the detected fluorescence, a lifetime of the detected fluorescence at each of the plurality of pixels, and pseudo-coloring the plurality of pixels based on the lifetime of the detected fluorescence at each of the plurality of pixels. Operation 906 may be performed in any of the ways described herein.

The systems and methods described herein have been described with reference to fluorescence. However, it will be appreciated that the systems and methods described herein are not limited to fluorescence, but may be applied to any other type of luminescence, including but not limited to photoluminescence (e.g., phosphorescence, etc.), electroluminescence, chemiluminescence, mechanoluminescence, radioluminescence, and the like.

In some examples, a non-transitory computer-readable medium storing computer-readable instructions may be provided in accordance with the principles described herein.

The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 10:
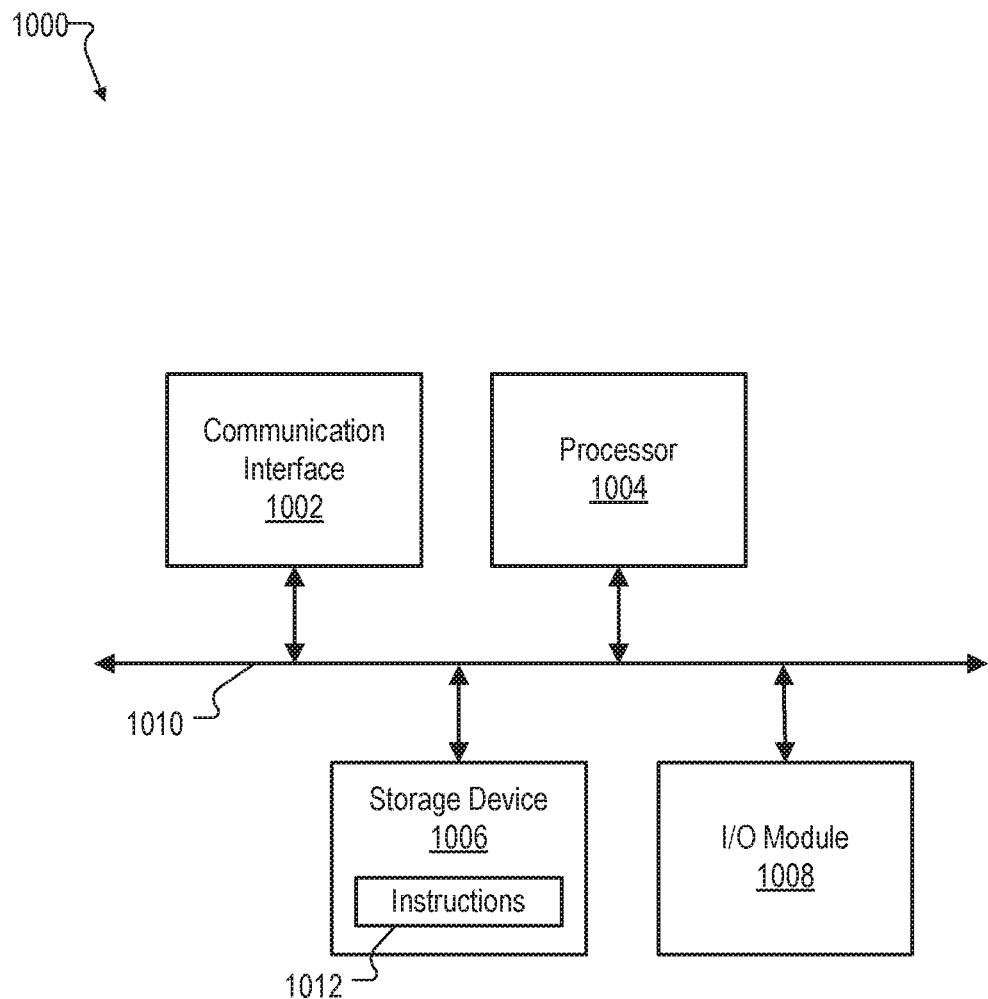
FIG. 10 illustrates an exemplary computing device according to principles described herein.

FIG. 10 illustrates an exemplary computing device 1000 that may be specifically configured to perform one or more of the processes described herein. Any of the systems, units, computing devices, and/or other components described herein may be implemented by computing device 1000.

As shown in FIG. 10, computing device 1000 may include a communication interface 1002, a processor 1004, a storage device 1006, and an input/output ("I/O") module 1008 communicatively connected one to another via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data and/or interpreting, executing, and/or directing execution of one or more of the instructions, processes, and/or operations described herein. Processor 1004 may perform operations by executing computer-executable instructions 1012 (e.g., an application, software, code, and/or other executable data instance) stored in storage device 1006.

Storage device 1006 may include one or more data storage media, devices, or configurations and may employ any type, form, and combination of data storage media and/or device. For example, storage device 1006 may include, but is not limited to, any combination of the non-volatile media and/or volatile media described herein. Electronic data, including data described herein, may be temporarily and/or permanently stored in storage device 1006. For example, data representative of computer-executable instructions 1012 configured to direct processor 1004 to perform any of the operations described herein may be stored within storage device 1006. In some examples, data may be arranged in one or more databases residing within storage device 1006.

I/O module 1008 may include one or more I/O modules configured to receive user input and provide user output. I/O module 1008 may include any hardware, firmware, software, or combination thereof supportive of input and output capabilities. For example, I/O module 1008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
  direct, during a surgical procedure performed with a computer-assisted surgical system, an illumination source included in the computer-assisted surgical system to illuminate a scene associated with the surgical procedure with fluorescence excitation illumination configured to excite a fluorophore present at the scene,
  direct an imaging device included in the computer-assisted surgical system to detect, during the surgical procedure, fluorescence emitted by the fluorophore in response to excitation of the fluorophore by the fluorescence excitation illumination, wherein:
    the imaging device comprises a detector having a plurality of distinct regions each configured to detect the fluorescence emitted by the fluorophore, and
    the directing the imaging device to detect the fluorescence comprises directing the plurality of distinct regions to sample the fluorescence in succession over a time period that is less than a lifetime of the fluorescence to generate a plurality of fluorescence image signals, each region included in the plurality of distinct regions generating a distinct fluorescence image signal included in the plurality of fluorescence image signals,
  determine, based on the plurality of fluorescence image signals, the lifetime of the fluorescence,
  determine, based on the determined lifetime of the fluorescence, an identity of the fluorophore, and
  configure, during the surgical procedure and based on the determined identity of the fluorophore, operation of the computer-assisted surgical system.

2. The system of claim 1, wherein the processor is configured to determine the identity of the fluorophore by:
   accessing a lookup table comprising fluorophore data representative of a fluorescence lifetime of fluorescence emitted by each of a plurality of fluorophores, the plurality of fluorophores including the fluorophore present at the scene, and
   selecting, from among the plurality of fluorophores, a particular fluorophore that emits fluorescence having a fluorescence lifetime that best matches the determined lifetime of the fluorescence emitted by the fluorophore present at the scene.

3. The system of claim 1, wherein the configuring the operation of the computer-assisted surgical system comprises setting, based on the identity of the fluorophore, a configuration of the fluorescence excitation illumination.

4. The system of claim 1, wherein the configuring the operation of the computer-assisted surgical system comprises setting, based on the identity of the fluorophore, a configuration of the imaging device.

5. The system of claim 4, wherein the configuration of the imaging device specifies at least one of a sampling rate of the imaging device, an exposure time of the imaging device, and a gain of the imaging device.

6. The system of claim 1, wherein the configuring the operation of the computer-assisted surgical system comprises:
   generating, based on the detected fluorescence, a fluorescence image for presentation by a display device communicatively coupled to the processor, and
   configuring, based on the identity of the fluorophore, the display of the fluorescence image.

7. The system of claim 1, wherein:
   the fluorescence excitation illumination is further configured to excite an additional fluorophore present at the scene, and
   the processor is further configured to execute the instructions to:
      direct the imaging device to detect, during the surgical procedure, additional fluorescence emitted by the additional fluorophore in response to excitation of the additional fluorophore by the fluorescence excitation illumination,
      determine, based on the detected additional fluorescence, a lifetime of the additional fluorescence, and
      determine, based on the determined lifetime of the additional fluorescence, an identity of the additional fluorophore.

8. A system comprising:
   a memory storing instructions; and
   a processor communicatively coupled to the memory and configured to execute the instructions to:
      direct an illumination source to illuminate a scene with fluorescence excitation illumination configured to excite a fluorophore present at the scene,
      direct an imaging device to detect fluorescence emitted by the fluorophore in response to excitation of the fluorophore by the fluorescence excitation illumination, wherein:
         the imaging device comprises a detector having a plurality of distinct regions each configured to detect the fluorescence emitted by the fluorophore, and
         the directing the imaging device to detect the fluorescence comprises directing the plurality of distinct regions to sample the fluorescence in succession over a time period that is less than a lifetime of the fluorescence to generate a plurality of fluorescence image signals, each region included in the plurality of distinct regions generating a distinct fluorescence image signal included in the plurality of fluorescence image signals, and
      generate, based on the detected fluorescence, a fluorescence image comprising a plurality of pixels, the generating of the fluorescence image comprising:
         determining, based on the plurality of fluorescence image signals, the lifetime of the detected fluorescence at each of the plurality of pixels, and
         pseudo-coloring the plurality of pixels based on the lifetime of the detected fluorescence at each of the plurality of pixels.

9. The system of claim 8, wherein the pseudo-coloring comprises applying a color scale that specifies colors corresponding to values fluorescence lifetime values.

10. The system of claim 8, wherein the processor is further configured to determine, based on the lifetime of the detected fluorescence at a region of pixels included in the plurality of pixels, a tissue type of the tissue in which the fluorophore is present.

11. The system of claim 10, wherein the processor is further configured to configure, based on the determined tissue type, a display of the fluorescence image.

12. A method comprising:
   directing, by a fluorescence imaging control system during a surgical procedure performed with a computer-assisted surgical system, an illumination source included in the computer-assisted surgical system to illuminate a scene associated with the surgical procedure with fluorescence excitation illumination configured to excite a fluorophore present at the scene;
   directing, by the fluorescence imaging control system, an imaging device included in the computer-assisted surgical system to detect, during the surgical procedure, fluorescence emitted by the fluorophore in response to excitation of the fluorophore by the fluorescence excitation illumination, wherein:
      the imaging device comprises a detector having a plurality of distinct regions each configured to detect the fluorescence emitted by the fluorophore, and
      the directing the imaging device to detect the fluorescence comprises directing the plurality of distinct regions to sample the fluorescence in succession over a time period that is less than a lifetime of the fluorescence to generate a plurality of fluorescence image signals, each region included in the plurality of distinct regions generating a distinct fluorescence image signal included in the plurality of fluorescence image signals;
   determining, by the fluorescence imaging control system based on the plurality of fluorescence image signals, a lifetime of the fluorescence;
   determining, by the fluorescence imaging control system based on the determined lifetime of the fluorescence, an identity of the fluorophore, and
   configuring, by the fluorescence imaging control system during the surgical procedure and based on the determined identity of the fluorophore, operation of the computer-assisted surgical system.

13. The method of claim 12, wherein the determining of the identity of the fluorophore comprises:
   accessing a lookup table comprising fluorophore data representative of a fluorescence lifetime of fluorescence emitted by each of a plurality of fluorophores, the plurality of fluorophores including the fluorophore present at the scene, and selecting, from among the plurality of fluorophores, a particular fluorophore that emits fluorescence having a fluorescence lifetime that best matches the determined lifetime of the fluorescence emitted by the fluorophore present at the scene.

14. The method of claim 12, wherein the configuring the operation of the computer-assisted surgical system comprises:

setting, based on the identity of the fluorophore, a configuration of the fluorescence excitation illumination.

15. The method of claim 12, wherein the configuring the operation of the computer-assisted surgical system comprises:

setting, based on the identity of the fluorophore, a configuration of the imaging device.

16. The method of claim 15, wherein the configuration of the imaging device specifies at least one of a sampling rate of the imaging device, an exposure time of the imaging device, and a gain of the imaging device.

17. The method of claim 12, wherein the configuring the operation of the computer-assisted surgical system comprises:

generating, based on the detected fluorescence, a fluorescence image for presentation by a display device, and configuring, based on the identity of the fluorophore, the display of the fluorescence image.

18. The system of claim 1, wherein the processor is further configured to execute the instructions to determine, based on one or more additional properties of the fluorophore, the identity of the fluorophore.

19. The system of claim 7, wherein:

the fluorescence excitation illumination comprises a first set of pulses of fluorescence excitation illumination having a first wavelength configured to excite the fluorophore and a second set of pulses of fluorescence excitation illumination having a second wavelength configured to excite the additional fluorophore, wherein the first wavelength is different from the second wavelength;

the directing the imaging device to detect the fluorescence comprises directing the imaging device to detect the fluorescence in sync with the first set of pulses; and the directing the imaging device to detect the additional fluorescence comprises directing the imaging device to detect the additional fluorescence in sync with the second set of pulses.

20. The system of claim 1, wherein the directing each region included in the plurality of distinct regions to sample the fluorescence in succession over the time period comprises activating each region of the plurality of distinct regions in succession over the time period.

* * * * *